(12) United States Patent
Margolis et al.

(10) Patent No.: US 8,946,243 B2
(45) Date of Patent: Feb. 3, 2015

(54) COMPOUNDS AND METHODS FOR THE TREATMENT OF VIRAL INFECTION

(75) Inventors: Leonid Margolis, Kensington, MD (US); Jan Balzarini, Leuven (BE); Christopher McGuigan, Cardiff (GB); Andrea Lisco, Washington, DC (US); Christophe Vanpouille, Bethesda, MD (US); Marco Derudas, Sassari (IT)

(73) Assignees: The United States of America, as represented by the Secretary, Department of Health and Human Services, Washington, DC (US); Katholieke Universiteit Leuven, Leuven (BE)

( * ) Notice: Subject to any disclaimer, the term of this patent is extended or adjusted under 35 U.S.C. 154(b) by 1003 days.

(21) Appl. No.: 12/934,769

(22) PCT Filed: Mar. 27, 2009

(86) PCT No.: PCT/US2009/038644
§ 371 (c)(1),
(2), (4) Date: Apr. 12, 2011

(87) PCT Pub. No.: WO2009/142827
PCT Pub. Date: Nov. 26, 2009

(65) Prior Publication Data
US 2011/0184003 A1    Jul. 28, 2011

Related U.S. Application Data

(60) Provisional application No. 61/040,640, filed on Mar. 28, 2008, provisional application No. 61/044,482, filed on Apr. 12, 2008.

(51) Int. Cl.
*A61K 31/522* (2006.01)
*C07D 473/18* (2006.01)
*C07F 9/6561* (2006.01)

(52) U.S. Cl.
CPC ................................ *C07F 9/65616* (2013.01)
USPC ..................................... 514/263.33; 544/276

(58) Field of Classification Search
CPC  C07D 473/00; C07D 473/18; C07F 9/65616; A61K 32/522
USPC ............................................ 544/276; 514/81
See application file for complete search history.

(56) References Cited

PUBLICATIONS

Wermuth, Camille. "Molecular Variations Based on Isoteric Replacements." The Practice of Medicinal Chemistry. Academic Press, 1996. pp. 203-237.*
Congiatu, C. Nucleosides, Nucleotides, and Nucleic Acids, 24 5-7 (2005) 485-489.*
Banker, Gilbert S. Modern Pharmaceutics 3rd ed. Marcel Dekker, Inc. New York, 1996.*
Balzarini J. et al., "Antiviral activity of cyclosaligenyl prodrugs of acyclovir, carbovir and abacavir", Antivir Chem Chemother. Sep. 2001;12(5):301-6.
Biancotto A., et al., "Abnormal activation and cytokine spectra in lymph nodes of people chronically infected with HIV-1", Blood. May 15, 2007;109(10):4272-9. Epub Feb. 8, 2007.
Chen T. et al., "Anatomical mapping of human herpesvirus reservoirs of infection", Mod Pathol. May 2006;19(5):726-37.
Corey L., "Synergistic copathogens—HIV-1 and HSV-2", N Engl J Med. Feb. 22, 2007;356(8):854-6.
De Bolle L. et al., "Update on human herpesvirus 6 biology, clinical features, and therapy", Clin Microbiol Rev. Jan. 2005;18(1):217-45.
De Clercq, E. et al., "Antiviral agents active against human herpesviruses HHV-6, HHV-7 and HHV-8", Rev Med Virol. Nov.-Dec. 2001;11(6):381-95.
Elion, G.B., "The biochemistry and mechanism of action of acyclovir", J Antimicrob Chemother. Sep. 1983;12 Suppl B:9-17.
Glushakova, S. et al., "Infection of human tonsil histocultures: a model for HIV pathogenesis", Nat Med. Dec. 1995;1(12):1320-2.
Gorelick R.J. et al., "Noninfectious human immunodeficiency virus type 1 mutants deficient in genomic RNA", J Virol. Jul. 1990;64(7):3207-11.
Grivel, J.C. et al., "HIV-1 pathogenesis differs in rectosigmoid and tonsillar tissues infected ex vivo with CCR5- and CXCR4-tropic HIV-1", AIDS. Jun. 19, 2007;21(10):1263-72.
Grivel, J.C. et al., "Suppression of CCR5- but not CXCR4-tropic HIV-1 in lymphoid tissue by human herpesvirus 6", Nat Med. Nov. 2001;7(11):1232-5.
Ioannidis, J.P. et al., "Clinical efficacy of high-dose acyclovir in patients with human immunodeficiency virus infection: a meta-analysis of randomized individual patient data", J Infect Dis. Aug. 1998;178(2):349-59.
Lisco A., et al., "Viral interactions in human lymphoid tissue: Human herpesvirus 7 suppresses the replication of CCR5-tropic human immunodeficiency virus type 1 via CD4 modulation", J Virol. Jan. 2007;81(2):708-17. Epub Oct. 25, 2006.
Lusso P. et al., Human herpesvirus 6 in AIDS. Lancet. Mar. 5, 1994;343(8897):555-6.
Margolis L., "Cytokines—strategic weapons in germ warfare?" Nat Biotechnol. Jan. 2003;21(1):15-6.
Mcguigan C. et al., "Synthesis and antiviral activity of acyclovir-5'-(phenyl methoxy alaninyl)phosphate as a possible membrane-soluble nucleotide prodrug" Bioorganic & Medicinal Chemistry Letters, Pergamon, Elsevier Science, GB, vol. 10, No. 7, Apr. 1, 2000, pp. 645-647, XP004191845.
Mcguigan C. et al., "Successful kinase bypass with new acyclovir phosphoramidate prodrugs" Bioorganic & Medicinal Chemistry Letters, Pergamon, Elsevier Science, GB, vol. 18, No. 15, Jun. 24, 2008, pp. 4364-4367, XP023180558.
Nagot N. et al., "ANRS 1285 Study Group. Reduction of HIV-1 RNA levels with therapy to suppress herpes simplex virus", N Engl J Med. Feb. 22, 2007;356(8):790-9.
Reardon J.E. et al., "Herpes simplex virus type 1 DNA polymerase. Mechanism of inhibition by acyclovir triphosphate", J Biol Chem. May 5, 1989;264(13):7405-11.

(Continued)

*Primary Examiner* — Golam M M Shameem
*Assistant Examiner* — Laura Daniel

(57) ABSTRACT

The invention relates to compounds and methods for treating or preventing a viral infection, by administering a monophosphorylated prodrug of acyclovir or monophosphorylated derivative of an acyclovir prodrug to a subject suffering from or susceptible (to a viral infection, such as HIV infection.

12 Claims, 1 Drawing Sheet

(56) References Cited

PUBLICATIONS

Resnick L. et al., "In vitro suppression of HTLV-III/LAV infectivity by a combination of acyclovir and suramin", J Infect Dis. Dec. 1986;154(6):1027-30.

Schacker T. et al., "Changes in plasma human immunodeficiency virus type 1 RNA associated with herpes simplex virus reactivation and suppression", J Infect Dis. Dec. 15, 2002;186(12):1718-25. Epub Nov. 22, 2002.

Soul-Lawton J. et al., "Absolute bioavailability and metabolic disposition of valaciclovir, the L-valyl ester of acyclovir, following oral administration to humans", Antimicrob Agents Chemother. Dec. 1995;39(12):2759-64.

St Clair, M.H. et al., "Inhibition of cellular alpha and virally induced deoxyribonucleic acid polymerases by the triphosphate of acyclovir", Antimicrob Agents Chemother. Nov. 1980;18(5):741-5.

Suligoi B. et al., "Italian Seroconversion Study. No protective effect of acyclovir on HIV disease progression in a cohort of HSV-2-HIV-infected individuals", Antivir Ther. Dec. 2002;7(4):289-91.

Talarico, C.L. et al., "Acyclovir is phosphorylated by the human cytomegalovirus UL97 protein. Antimicrob Agents Chemother," Aug. 1999;43(8):1941-6.

Torres R.A. et al., "Acyclovir use and survival among human immunodeficiency virus-infected patients with CD4 cell counts of < 500/mm3. The Terry Beirn Community Programs for Clinical Research on AIDS (CPCRA)", Clin Infect Dis. Jan. 1998;26(1):85-90.

Xiang J. et al., "Effect of coinfection with GB virus C on survival among patients with HIV infection", N Engl J Med. Sep. 6, 2001;345(10):707-14.

Zuckerman R.A. et al., "Herpes simplex virus (HSV) suppression with valacyclovir reduces rectal and blood plasma HIV-1 levels in HIV-1/HSV-2-seropositive men: a randomized, double-blind, placebo-controlled crossover trial", J Infect Dis. Nov. 15, 2007;196(10):1500-8. Epub Oct. 31, 2007.

Uchida et al., "In Vitro Anti-Human Immunodeficiency Virus Activities of Z- and E-Methylenecyclopropane Nucleoside Analogues and Their Phosphoro-L-Alaninate Diesters", Antimicrob Agents Chemother, Jun. 1999, 43(6):1487-1490.

* cited by examiner

Figure 1
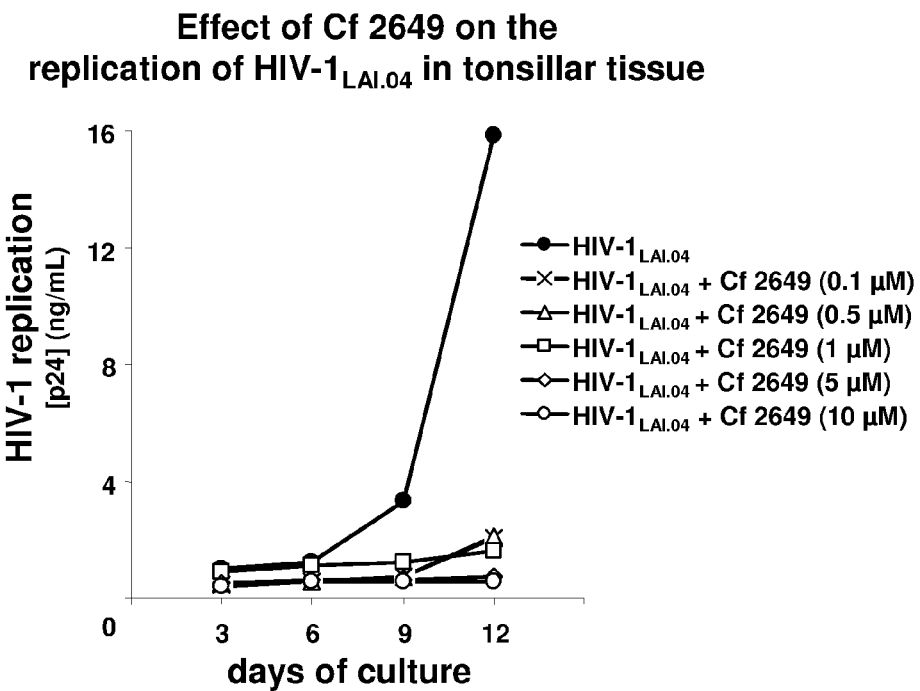
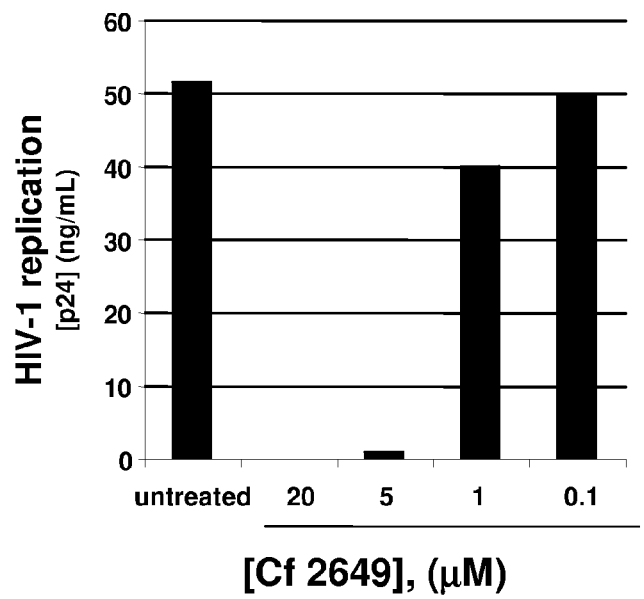
Figure 2

COMPOUNDS AND METHODS FOR THE TREATMENT OF VIRAL INFECTION

CROSS-REFERENCE TO RELATED APPLICATIONS

This application is the National Stage of International Application No. PCT/US2009/038644, filed Mar. 27, 2009, which claims the benefit of U.S. Provisional Application No. 61/040,640, filed Mar. 28, 2008, and U.S. Provisional Application No. 61/044,482, filed Apr. 12, 2008, the disclosures of which are incorporated herein by reference in their entireties.

STATEMENT OF U.S. GOVERNMENT INTEREST

Funding for the present invention was provided in part by support from the Intramural Research Program of the National Institute of Child Health and Human Development, the U.S. National Institutes of Health, and by federal funds from the National Cancer Institute, a component of the U.S. National Institutes of Health, under contract NO1-CO-12400. Accordingly, the Government of the United States has certain rights in and to the invention.

BACKGROUND OF THE INVENTION

The human immunodeficiency virus HIV-1 is characterized by a very high mutation frequency. Because the virus mutates so frequently, drug resistance to antiviral therapies s is an ongoing challenge. Common regimens of anti-HIV drugs include Nucleoside Reverse Transcriptase Inhibitors (NRTIs) that mimic thymidine (AZT, stavudine), deoxycytidine (Lamivudine, Emtricitabine) or deoxyguanosine (Abacavir) nucleosides.

Acyclovir (ACV) is a deoxyguanosine analogue particularly active against α-herpesiviruses HHV-1, HHV-2, and HHV-3 (respectively known as herpes simplex viruses 1 and 2 and varicella zoster virus). ACV is phosphorylated in herpesvirus-infected cells by a viral kinase. The resulting monophosphate is then converted into ACV triphosphate (ACV-TP) by cellular enzymes and is subsequently incorporated in the nascent viral DNA chain, causing its obligate termination. Moreover, the incorporated ACV-TP causes the viral DNA polymerase to become irreversibly bound to the terminated chain.

SUMMARY OF THE INVENTION

In one aspect, the invention provides a compound represented by the formula (Formula I):

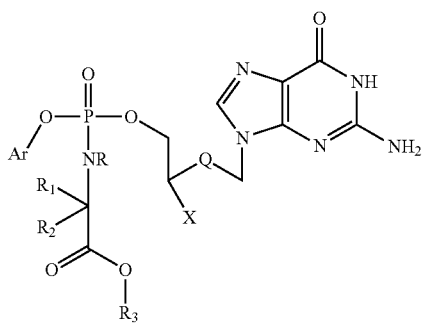

(I)

wherein:

Ar is an aryl group having 6 to 30 carbon atoms or a heteroaryl group having 6 to 30 atoms, wherein the aryl or heteroaryl group may be substituted with 1-3 substituents; Q is O, S, or $CR_4R_5$, wherein $R_4$ and $R_5$ are independently selected from H and $C_1$-$C_6$ alkyl;

X is H, or $CH_2OH$;

$R_1$ and $R_2$ are independently selected from H, or the group consisting of optionally substituted $C_1$-$C_{20}$ alkyl, $C_2$-$C_{20}$ alkenyl, $C_{1-20}$ alkoxy, $C_2$-$C_{20}$ alkynyl, or $C_3$-$C_{20}$ cycloalkyl; or $R_1$ and $R_2$ are fused to form a contiguous carbocyclic or heterocyclic ring which may be 3-20 members in total;

each of R and $R_3$ is independently selected from the group consisting of H, and optionally substituted $C_1$-$C_{20}$ alkyl, $C_3$-$C_{20}$ cycloalkyl, $C_2$-$C_{20}$ alkenyl, $C_{1-20}$ alkoxy, or $C_6$-$C_{30}$ alkynyl; or R and $R_1$ are taken together with the carbon and nitrogen atoms to which they are respectively attached to form a 4-6 membered ring;

and pharmaceutically acceptable salts, solvates, and prodrugs thereof;

with the proviso that if Ar is phenyl, R is H, $R_1$ is methyl, $R_2$ is H, $R_3$ is H or methyl, and X is H, then Q cannot be O.

In certain embodiments, R and $R_1$ are taken together with the nitrogen and carbon atoms to which they are respectively attached to form a 5 membered ring. In certain embodiments, Ar is phenyl, pyridinyl, pyrimidinyl, or naphthyl. In certain embodiments, Ar is phenyl, or 1-naphthyl. In certain embodiments, Ar is phenyl. In certain embodiments, X is H. In certain embodiments, Q is $CH_2$. In certain embodiments, $R_3$ is not H. In certain embodiments, $R_3$ is optionally substituted $C_1$-$C_{20}$ alkyl or $C_3$-$C_{20}$ cycloalkyl. In certain embodiments, $R_3$ is methyl, ethyl, n-propyl, i-propyl, 2-butyl or benzyl. In certain embodiments, $R_1$ is the sidechain of a naturally-occurring amino acid. In certain embodiments, $R_1$ is not methyl, but in certain embodiments, $R_1$ is methyl. In certain embodiments, the stereochemistry at the phosphorus atom is Rp or Sp.

In certain embodiments, the compound is acyclovir 5'-O-(1-naphthyl benzylalaninyl)phosphate, acyclovir 5'-O-(1-naphthyl n-propylalaninyl)phosphate, acyclovir 5'-O-(1-phenyl benzylalaninyl)phosphate, acyclovir 5'-O-(1-naphthyl methylalaninyl)phosphate, or acyclovir 5'-O-(1-phenyl benzylphenylalaninyl)phosphate.

In another aspect, the invention provides a pharmaceutical formulation comprising a compound of Formula I, together with a pharmaceutically acceptable carrier.

In another aspect, the invention provides a method for treating or preventing a viral infection, the method including the step of administering a monophosphorylated prodrug of acyclovir or monophosphorylated derivative of an acyclovir prodrug to a subject suffering from or susceptible to a viral infection. In certain embodiments, the viral infection is an HIV infection. In certain embodiments, the subject (or a cell or tissue of the subject) is not infected with a herpesvirus (e.g., is not infected with HHV-1, HHV-2, or HHV-3); however, in certain embodiments, the subject is infected with a herpes virus.

In one embodiment, the invention provides a method for treating or preventing HIV infection, the method including the step of administering to a subject suffering from or susceptible to HIV infection a compound represented by Formula I or the formula (Formula IA):

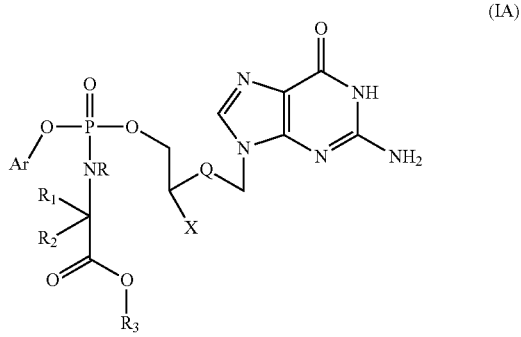

(IA)

wherein:
wherein Ar is an aryl group having 6 to 30 carbon atoms or a heteroaryl group having 6 to 30 atoms, wherein the aryl or heteroaryl group may be substituted with 1-3 substituents;

Q is O, S, or $CR_4R_5$, wherein $R_4$ and $R_5$ are independently selected from H and $C_1$-$C_6$ alkyl;

X is H, or $CH_2OH$;

$R_1$ and $R_2$ are independently selected from H, or the group consisting of optionally substituted $C_1$-$C_{20}$ alkyl, $C_2$-$C_{20}$ alkenyl, $C_{1-20}$ alkoxy, $C_2$-$C_{20}$ alkynyl, or $C_3$-$C_{20}$ cycloalkyl; or $R_1$ and $R_2$ are fused to form a contiguous carbocyclic or heterocyclic ring which may be 3-20 members in total;

each of R and $R_3$ is independently selected from the group consisting of H, and optionally substituted $C_1$-$C_{20}$ alkyl, $C_3$-$C_{20}$ cycloalkyl, $C_2$-$C_{20}$ alkenyl, $C_{1-20}$ alkoxy, or $C_6$-$C_{30}$ alkynyl; or R and $R_1$ are taken together with the carbon and nitrogen atoms to which they are respectively attached to form a 4-6 membered ring; and pharmaceutically acceptable salts, solvates, and prodrugs thereof; such that the viral infection is treated or prevented.

In another aspect, the invention provides a process for the preparation of a monophosphorylated prodrug of acyclovir or monophosphorylated derivative of an acyclovir prodrug, the method comprising reacting a suitably protected acyclic nucleoside analogue with a suitable phosphorus reagent, such as a phosphorochloridate, in the presence of suitable catalyst or base, optionally followed by appropriate deprotection steps.

In still another aspect, the invention provides a kit. The kit can be used for the treatment or prevention of HIV infection. The kit includes a therapeutically effective amount of an acylcovir prodrug as described herein, together with instructions for administation of the acyclovir prodrug to a subject in need thereof, such that HIV infection is treated or prevented.

In still another aspect, the invention relates to the use of an acyclovir prodrug as described herein for the manufacture of a medicament for the treatment or prevention of HIV infection.

BRIEF DESCRIPTION OF THE DRAWINGS

FIG. 1 is a graph showing the time course of the suppression of HIV-1 replication by the ACV prodrug Cf 2649 in human lymphoid tissue ex vivo. 27 blocks of human tonsillar tissue were inoculated with HIV-1 isolate LAI.04 and treated with the ACV prodrug CF2649 at the concentrations indicated in the legend. Cf 2649 was replenished every three days with a medium change. HIV-1 replication was evaluated by p24 ELISA. Note efficient suppression of HIV replication by the drug.

FIG. 2 is a graph showing the dose-dependency of HIV-suppression by the ACV prodrug Cf 2649 in MT4 cells. T cells of MT4 cell line were infected with HIV-1 isolate LAI.04 and treated with the ACV prodrug CF2649 at the concentrations indicated on the X axis. HIV-1 replication was evaluated at day 3 post-infection by p24 ELISA. Note suppression of HIV replication by the drug in dose-dependent manner.

DETAILED DESCRIPTION OF THE INVENTION

The present invention is related, at least in part, to the discovery that ACV triphosphate (ACV-TP), the active form of ACV generated in cells infected with one or more herpesviruses, is a potent inhibitor of HIV-1 RT. The present invention relates to compounds and method for treatment of HIV infection by bypassing the herpes virus thymidine kinase requirement for activation of ACV by synthesizing a new class of monophosphorylated ACV prodrugs or derivatives. The invention also contemplates monophosphorylated prodrugs or derivatives of additional acyclic nucleoside compounds such as ganciclovir.

DEFINITIONS

The term "monophosphorylated prodrug of acyclovir or monophosphorylated derivative of an acyclovir prodrug" refers to a derivative of acyclovir or a derivative of an acyclovir prodrug that contains at least one covalently bound phosphate group which can be converted in vivo to a triphosphate. The invention also contemplates monophosphorylated prodrugs or derivatives of additional acyclic nucleoside compounds such as ganciclovir.

The term "subject" refers to animals such as mammals, including, but not limited to, primates (e.g., humans), cows, sheep, goats, horses, dogs, cats, rabbits, rats, mice and the like. In certain embodiments, the subject is a human.

The term "prodrug" means a derivative of a compound that can hydrolyze, oxidize, or otherwise react under biological conditions (in vitro or in vivo) to provide a compound of this invention. Prodrugs may only become active upon such reaction under biological conditions, but they may have activity in their unreacted forms. Examples of prodrugs contemplated in this invention include, but are not limited to, analogs or derivatives of a compound of formula I or IA that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. In another example, a 2-amino-6-methoxy-purin-9-yl moiety can be converted to a 2-aminopurine moiety in vivo. Prodrugs can typically be prepared using well-known methods, such as those described by 1 BURGER'S MEDICINAL CHEMISTRY AND DRUG DISCOVERY (1995) 172-178, 949-982 (Manfred E. Wolff ed., 5$^{th}$ ed), the entire teachings of which are incorporated herein by reference.

The terms "biohydrolyzable amide", "biohydrolyzable ester", "biohydrolyzable carbamate", "biohydrolyzable carbonate", "biohydrolyzable ureide" and "biohydrolyzable phosphate analogue" mean an amide, ester, carbamate, carbonate, ureide, or phosphate analogue, respectively, that either: 1) does not destroy the biological activity of the compound and confers upon that compound advantageous properties in vivo, such as uptake, duration of action, or onset of action; or 2) is itself biologically inactive but is converted in vivo to a biologically active compound. Examples of biohydrolyzable amides include, but are not limited to, lower alkyl amides, α-amino acid amides, alkoxyacyl amides, and alkylaminoalkylcarbonyl amides. Examples of biohydrolyzable esters include, but are not limited to, lower alkyl esters, alkoxyacyloxy esters, alkyl acylamino alkyl esters, and choline esters. Examples of biohydrolyzable carbamates include, but are not limited to, lower alkylamines, substituted ethylenediamines, aminoacids, hydroxyalkylamines, heterocyclic and heteroaromatic amines, and polyether amines.

The term "aryl" means a monocyclic or polycyclic-aromatic ring or ring radical comprising carbon and hydrogen atoms. An aryl group can have 6 to 30 carbon atoms, e.g., 6-14, or 6-10 carbon atoms. Examples of suitable aryl groups include, but are not limited to, phenyl, tolyl, anthacenyl, fluorenyl, indenyl, azulenyl, and naphthyl, as well as benzo-fused carbocyclic moieties such as 5,6,7,8-tetrahydronaphthyl. An aryl group can be unsubstituted or substituted with one or more substituents (including without limitation alkyl (e.g., lower alkyl or alkyl substituted with one or more halo), hydroxy, alkoxy (e.g., lower alkoxy), alkylthio, cyano, halo, amino, and nitro. In certain embodiments, the aryl group is a monocyclic ring, wherein the ring comprises 6 carbon atoms.

As used herein, the term "alkyl" means a saturated straight chain or branched non-cyclic hydrocarbon typically having from 1 to 20 carbon atoms (more preferably 1 to 8, referred to herein as a lower alkyl). Representative saturated straight chain alkyls include methyl, ethyl, n-propyl, n-butyl, n-pentyl, n-hexyl, n-heptyl, and n-octyl; while saturated branched alkyls include isopropyl, sec-butyl, isobutyl, tert-butyl, isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, 2,3-dimethylpentyl, 2,4-dimethylpentyl, 2,3-dimethylhexyl, 2,4-dimethylhexyl, 2,5-dimethylhexyl, 2,2-dimethylpentyl, 2,2-dimethylhexyl, 3,3-dimethylpentyl, 3,3-dimethylhexyl, 2-ethylpentyl, 3-ethylpentyl, 2-ethylhexyl, 3-ethylhexyl, 4-ethylhexyl, 2-methyl-2-ethylpentyl, 2-methyl-3-ethylpentyl, and 2-methyl-4-ethylpentyl and the like. Alkyl groups included in compounds of this invention may be optionally substituted with one or more substituents (e.g., one to six, or one to three, substitutents). Examples of substituents include, but are not limited to, amino, alkylamino, alkoxy, alkylthio, oxo, halo, acyl, nitro, hydroxyl, cyano, aryl, alkylaryl, aryloxy, arylsulfanyl, arylamino, carbocyclyl, carbocyclyloxy, carbocyclylthio, carbocyclylamino, heterocyclyl, heterocyclyloxy, heterocyclylamino, heterocyclylthio, and the like. In addition, any carbon in the alkyl segment may be substituted with oxygen (=O), sulfur (=S), or nitrogen (=NR$^{22}$, wherein R$^{22}$ is —H, an alkyl, acetyl, or aralkyl).

The term "alkoxy," as used herein, refers to an alkyl group which is linked to another moiety though an oxygen atom. Alkoxy groups can be substituted or unsubstituted with one or more substituents (e.g., one to three substituents) as described herein for alkyl groups. The term "alkenyl" means a straight chain or branched hydrocarbon radical typically having from 2 to 20 (e.g., 2 to 8) carbon atoms and having at least one carbon-carbon double bond. Representative straight chain and branched alkenyls include vinyl, allyl, 1-butenyl, 2-butenyl, isobutylenyl, 1-pentenyl, 2-pentenyl, 3-methyl-1-butenyl, 1-methyl-2-butenyl, 2,3-dimethyl-2-butenyl, 1-hexenyl, 2-hexenyl, 3-hexenyl, 1-heptenyl, 2-heptenyl, 3-heptenyl, 1-octenyl, 2-octenyl, 3-octenyl, and the like. Alkenyl groups can be substituted or unsubstituted with one or more substituents (e.g., one to three substituents) as described herein for alkyl groups.

The term "alkynyl" means a straight chain or branched, hydrocarbonon radical typically having from 2 to 20 (e.g., 2 to 8) carbon atoms and having at lease one carbon-carbon triple bond. Representative straight chain and branched alkynyls include acetylenyl, propynyl, 1-butynyl, 2-butynyl, 1-pentynyl, 2-pentynyl, 3-methyl-1-butynyl, 4-pentynyl,-1-hexynyl, 2-hexynyl, 5-hexynyl, 1-heptynyl, 2-heptynyl, 6-heptynyl, 1-octynyl, 2-octynyl, 7-octynyl, 1-nonynyl, 2-nonynyl, 8-nonynyl, 1-decynyl, 2-decynyl, 9-decynyl and the like. Alkynyl groups can be substituted or unsubstituted with one or more substituents (e.g., one to three substituents) as described herein for alkyl groups.

The term "cycloalkyl" means a saturated, mono- or polycyclic alkyl radical typically having from 3 to 20 (e.g., 3 to 8) carbon atoms. Representative cycloalkyls include cyclopropyl, cyclobutyl, cyclopentyl, cyclohexyl, cycloheptyl, and cyclooctyl. A cycloalkyl group may be substituted with one or more substituents (e.g., one to three substituents) as described herein for alkyl groups.

The term "halogen" or "halo" means —F, —Cl, —Br or —I.

As used herein, the term "heteroaryl" means a monocyclic or polycyclic heteroaromatic ring (or radical thereof) comprising carbon atom ring members and one or more heteroatom ring members (such as, for example, oxygen, sulfur or nitrogen). Typically, the heteroaromatic ring has from 5 to about 14 ring members in which at least 1 ring member is a heteroatom selected from oxygen, sulfur and nitrogen. In another embodiment, the heteroaromatic ring is a 5 or 6 membered ring and may contain from 1 to about 4 heteroatoms. In another embodiment, the heteroaromatic ring system has a 7 to 14 ring members and may contain from 1 to about 7 heteroatoms. Representative heteroaryls include pyridyl, furyl, thienyl, pyrrolyl, oxazolyl, imidazolyl, indolizinyl, thiazolyl, isoxazolyl, pyrazolyl, isothiazolyl, pyridazinyl, pyrimidinyl, pyrazinyl, triazinyl, triazolyl, pyridinyl, thiadiazolyl, pyrazinyl, quinolyl, isoquniolyl, indazolyl, benzoxazolyl, benzofuryl, benzothiazolyl, indolizinyl, imidazopyridinyl, isothiazolyl, tetrazolyl, benzimidazolyl, benzoxazolyl, benzothiazolyl, benzothiadiazolyl, benzoxadiazolyl, indolyl, tetrahydroindolyl, azaindolyl, imidazopyridyl, qunizaolinyl, purinyl, pyrrolo[2,3]pyrimidyl, pyrazolo[3,4]pyrimidyl or benzo(b)thienyl and the like. Heteroaryl groups may be optionally substituted with one or more substituents (e.g., one to three substituents) as described herein for aryl groups.

It is also to be understood that the terminology used herein is for purposes of describing particular embodiments only, and is not intended to be limiting. As used in the specification and the appended claims, the singular forms "a", "an", and "the" include plural referents unless the context clearly indicates otherwise. Thus, for example, reference to "a peptide" includes multiple peptides, reference to "a spacer" includes two or more spacers.

Unless otherwise defined, all technical and scientific terms used herein have the same meaning as commonly understood by one of ordinary skill in the art to which this invention belongs. All publications, patent applications, patents, and other references mentioned herein are incorporated by reference.

In one aspect, the invention provides a compound of Formula I:

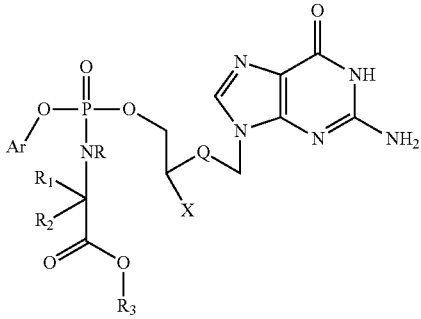

(I)

wherein:
wherein Ar is an aryl group having 6 to 30 carbon atoms or a heteroaryl group having 6 to 30 atoms, wherein the aryl or heteroaryl group may be substituted with 1-3 substituents;

Q is O, S, or $CR_4R_5$, wherein $R_4$ and $R_5$ are independently selected from H and $C_1$-$C_6$ alkyl;

X is H, or $CH_2OH$;

$R_1$ and $R_2$ are independently selected from H, or the group consisting of optionally substituted $C_1$-$C_{20}$ alkyl, $C_2$-$C_{20}$ alkenyl, $C_{1-20}$ alkoxy, $C_2$-$C_{20}$ alkynyl, or $C_3$-$C_{20}$ cycloalkyl; or $R_1$ and $R_2$ are fused to form a contiguous carbocyclic or heterocyclic ring which may be 3-20 members in total;

each of R and $R_3$ is independently selected from the group consisting of H, and optionally substituted $C_1$-$C_{20}$ alkyl, $C_3$-$C_{20}$ cycloalkyl, $C_2$-$C_{20}$ alkenyl, $C_{1-20}$ alkoxy, or $C_6$-$C_{30}$ alkynyl; or R and $R_1$ are taken together with the carbon and nitrogen atoms to which they are respectively attached to form a 4-6 membered ring;

and pharmaceutically acceptable salts, solvates, and prodrugs thereof;

with the proviso that if Ar is phenyl, R is H, $R_1$ is methyl, $R_2$ is H, $R_3$ is H or methyl, and X is H, then Q cannot be O.

In certain embodiments of Formulae I and IA, R and $R_1$ are taken together with the nitrogen and carbon atoms to which they are respectively attached to form a 5 membered ring (i.e., a pyrrolidine ring). In certain embodiments, Ar is phenyl, pyridinyl, pyrimidinyl, or naphthyl. In certain embodiments, Ar is phenyl, or 1-naphthyl. In certain embodiments, Ar is phenyl. In certain embodiments, Ar is naphthyl, e.g., 1-naphthyl. In certain embodiments, X is H. In certain embodiments, Q is $CH_2$. In certain embodiments, Q is O. In certain embodiments, $R_3$ is not H. In certain embodiments, $R_3$ is optionally substituted $C_1$-$C_{20}$ alkyl or $C_3$-$C_{20}$ cycloalkyl. In certain embodiments, $R_3$ is methyl, ethyl, n-propyl, i-propyl, 2-butyl or benzyl. In certain embodiments, $R_3$ is benzyl. In certain embodiments, $R_1$ is the sidechain of a naturally-occurring amino acid. In certain embodiments, $R_1$ has the L-configuration (i.e., e.g., the configuration of a naturally-occurring amino acid). In certain embodiments, $R_1$ is methyl. In certain embodiments, $R_1$ is phenylmethyl. In certain embodiments, $R_2$ is H. In certain embodiments, $R_1$ and $R_2$ are each alkyl, e.g., both methyl. In certain embodiments, $R_1$ and $R_2$ are each H. In certain embodiments, the stereochemistry at the phosphorus atom is Rp or Sp.

In certain embodiments, the compound is acyclovir 5'-O-(1-naphthyl benzylalaninyl)phosphate, acyclovir 5'-O-(1-naphthyl n-propylalaninyl)phosphate, acyclovir 5'-O-(1-phenyl benzylalaninyl)phosphate, acyclovir 5'-O-(1-naphthyl methylalaninyl)phosphate, or acyclovir 5'-O-(1-phenyl benzylphenylalaninyl)phosphate.

Without being bound by theory, it is believed that the compounds of Formula I or IA can readily penetrate into cells due to their lipophilic ester chains and thus are active in concentrations from 3 to 100 times lower than monophosphorylated ACV or ACV itself. At low concentrations, these prodrugs suppressed the replication of HIV-1 in MT-4 cells while non-phosphorylated ACV does not affect HIV-1 replication at all. For example, at a concentration of 5 µM, ACV prodrug Cf2649 inhibits replication of HIV-1 by 99% in the MT-4 cell line while both ACV-MP and ACV at the same concentration are inefficient in inhibiting HIV-1.

Moreover, these compounds may be efficient in preventing HIV transmission. Since the structure of these compounds is close to ACV, the low-toxicity drug that is used to treat herpes-virus infection, there is a strong possibility that they are non-toxic in vivo and have few if any significant side-effects. These drugs may be used in combination with other anti-HIV drugs. In particular, (i) application of these compounds topically (as microbicides) to the mucosa of HIV-infected persons will reduce the HIV viral load in their genital or rectal compartments thus reducing the probability of HIV transmission; (ii) topical application of these drugs to the mucosa of genitals or rectum (microbicides) to HIV-negative individuals may prevent transmission of HIV from an HIV-positive partner; (iii) given the inherent activity of ACV against HSV-2, the cause of frequently seen genital infections, the application of the ACV prodrugs will further decrease the incidence of HIV infection due to inhibition of HSV-2 infection; (iv) systemic application of these drugs may lead to control the HIV viral load in the plasmatic compartment thus achieving a major goal to reduce and slow down progression of the disease.

Thus, the present invention provides a method of treating HIV infection and Acquired Immune Deficiency Syndrome (AIDS).

Treatment of HIV Infection and AIDS

The invention provides methods of treatment for, or prevention of, HIV infections, which methods in general comprise administration of a therapeutically effective amount of a monophosphorylated prodrug of acyclovir (e.g., a compound of Formula I or IA) or a pharmaceutically acceptable salt, solvate, hydrate, or prodrug thereof to a subject such that HIV infection or AIDS is treated or prevented. Without wishing to be bound by any particular theory, it is believed that the monophosphorylated prodrugs of acyclovir is converted into an effective amount of acyclovir triphosphate.

In certain embodiments, monophosphorylated prodrugs of acyclovir or a pharmaceutically acceptable salt, solvate, hydrate, is administered to a subject (e.g., a mammal, e.g., a human) concurrently with one or more other biologically active agents. By "concurrently" it is meant that acyclovir or a pharmaceutically acceptable salt, solvate, hydrate, or prodrug thereof and the other agent are administered to a mammal in a sequence and within a time interval such that monophosphorylated prodrugs of acyclovir or a pharmaceutically acceptable salt, solvate, hydrate, or prodrug thereof can act together with the other agent to provide an increased or synergistic benefit than if they were administered otherwise. For example, each component may be administered at the same time or sequentially in any order at different points in time; however, if not administered at the same time, they should be administered sufficiently closely in time so as to provide the desired treatment effect. Preferably, all components are administered at the same time, and if not administered at the same time, they may all be administered from about 6 hours to about 12 hours apart from one another.

When used in combination with other therapeutic agents, monophosphorylated prodrugs of acyclovir or a pharmaceutically acceptable salt, solvate, hydrate, or prodrug thereof and the therapeutic agent can act additively or, more preferably, synergistically. In one embodiment, monophosphorylated prodrugs of acyclovir or a pharmaceutically acceptable salt, solvate, hydrate, or prodrug thereof is administered concurrently with another therapeutic agent in the same pharmaceutical composition. In another embodiment, monophosphorylated prodrugs of acyclovir or a pharmaceutically acceptable salt, solvate, hydrate, or prodrug thereof is administered concurrently with another therapeutic agent in separate pharmaceutical compositions. In still another embodiment, monophosphorylated prodrugs of acyclovir or a pharmaceutically acceptable salt, solvate, hydrate, or prodrug thereof is administered prior or subsequent to administration of another therapeutic agent. In one embodiment, combination therapy involves alternating between administering monophosphorylated prodrugs of acyclovir or a pharmaceutically acceptable salt, solvate, hydrate, or prodrug thereof and a pharmaceutical composition comprising another therapeutic agent, e.g., to minimize the toxicity associated with a particular drug. In certain embodiments, when monophosphorylated prodrugs of acyclovir or a pharmaceutically acceptable salt, solvate, hydrate, or prodrug thereof is administered concurrently with another therapeutic agent that potentially produces adverse side effects including, but not limited to toxicity, the therapeutic agent can advantageously be administered at a dose that falls below the threshold that the adverse side effect is elicited. In certain embodiments, a monophosphorylated prodrug of acyclovir or a pharmaceutically acceptable salt, solvate, hydrate, or prodrug thereof is administered concurrently with a second, and a third (and, optionally, a fourth) therapeutic agent (e.g., one or more agent(s) used for highly active antiretroviral therapy (HAART)).

Monophosphorylated prodrugs of acyclovir or a pharmaceutically acceptable salt, solvate, hydrate, or prodrug thereof may be used in combination with other medicaments such as nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, or HIV integrase inhibitors or combinations thereof. Without being so limited, monophosphorylated prodrugs of acyclovir or a pharmaceutically acceptable salt, solvate, hydrate, or prodrug thereof may be used in therapy in conjuction with reverse transcriptase inhibitors such as a dideoxynucleoside including AZT, ddI, ddC, d4T, 3TC, FTC, ABC, PMPA or TAT antagonists such as Ro 3-3335 and Ro 24-7429; protease inhibitors such as saquinavir, ritonavir, indinavir or AHG1343 (Viracept); NNRTIs such as nevirapine, delavirdine, efavirenz, TMC-125; fusion inhibitors such as enfuvirtide (T20); CCR5 inhibitors such as maraviroc; and other agents such as ganciclovir or pencyclovir, interferon, e.g., alpha-interon or interleukin II, or in conjunction with other immune modulation agents including bone marrow or lymphocyte transplants or other medications such as levamisol or thymosin which would increase lymphocyte numbers and/or function as is appropriate.

Monophosphorylated prodrugs of acyclovir or a pharmaceutically acceptable salt, solvate, hydrate, or prodrug thereof can be administered or formulated in combination with antibiotics. For example, they can be formulated with a macrolide (e.g., tobramycin (TOBI®)), a cephalosporin (e.g., cephalexin (KEFLEX®), cephradine (VELOSEF®), cefuroxime (CEFTIN®), cefprozil (CEFZIL®), cefaclor (CECLOR®), cefixime (SUPRAX®) or cefadroxil (DURICEF®)), a clarithromycin (e.g., clarithromycin (BIAXIN®)), an erythromycin (e.g., erythromycin (Emycin®)), a penicillin (e.g., penicillin V (V-CILLIN K® or PEN VEE K®)) or a quinolone (e.g., ofloxacin (FLOXIN®), ciprofloxacin (CIPRO®) or norfloxacin (NOROXIN®)), aminoglycoside antibiotics (e.g., apramycin, arbekacin, bambermycins, butirosin, dibekacin, neomycin, neomycin, undecylenate, netilmicin, paromomycin, ribostamycin, sisomicin, and spectinomycin), amphenicol antibiotics (e.g., azidamfenicol, chloramphenicol, florfenicol, and thiamphenicol), ansamycin antibiotics (e.g., rifamide and rifampin), carbacephems (e.g., loracarbef), carbapenems (e.g., biapenem and imipenem), cephalosporins (e.g., cefaclor, cefadroxil, cefamandole, cefatrizine, cefazedone, cefozopran, cefpimizole, cefpiramide, and cefpirome), cephamycins (e.g., cefbuperazone, cefmetazole, and cefminox), monobactams (e.g., aztreonam, carumonam, and tigemonam), oxacephems (e.g., flomoxef, and moxalactam), penicillins (e.g., amdinocillin, amdinocillin pivoxil, amoxicillin, bacampicillin, benzylpenicillinic acid, benzylpenicillin sodium, epicillin, fenbenicillin, floxacillin, penamccillin, penethamate hydriodide, penicillin o-benethamine, penicillin 0, penicillin V, penicillin V benzathine, penicillin V hydrabamine, penimepicycline, and phencihicillin potassium), lincosamides (e.g., clindamycin, and lincomycin), amphomycin, bacitracin, capreomycin, colistin, enduracidin, enviomycin, tetracyclines (e.g., apicycline, chlortetracycline, clomocycline, and demeclocycline), 2,4-diaminopyrimidines (e.g., brodimoprim), nitrofurans (e.g., furaltadone, and furazolium chloride), quinolones and analogs thereof (e.g., cinoxacin, clinafloxacin, flumequine, and grepagloxacin), sulfonamides (e.g., acetyl sulfamethoxypyrazine, benzylsulfamide, noprylsulfamide, phthalylsulfacetamide, sulfachrysoidine, and sulfacytine), sulfones (e.g., diathymosulfone, glucosulfone sodium, and solasulfone), cycloserine, mupirocin and tuberin.

Monophosphorylated prodrugs of acyclovir or a pharmaceutically acceptable salt, solvate, hydrate can also be administered or formulated in combination with an antiemetic agent. Suitable antiemetic agents include, but are not limited to, metoclopromide, domperidone, prochlorperazine, promethazine, chlorpromazine, trimethobenzamide, ondansetron, granisetron, hydroxyzine, acethylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinols, thiethylperazine, thioproperazine, tropisetron, and mixtures thereof.

Monophosphorylated prodrugs of acyclovir or a pharmaceutically acceptable salt, solvate, hydrate can be administered or formulated in combination with an antidepressant. Suitable antidepressants include, but are not limited to, binedaline, caroxazone, citalopram, dimethazan, fencamine, indalpine, indeloxazine hydrocholoride, nefopam, nomifensine, oxitriptan, oxypertine, paroxetine, sertraline, thiazesim, trazodone, benmoxine, iproclozide, iproniazid, isocarboxazid, nialamide, octamoxin, phenelzine, cotinine, rolicyprine, rolipram, maprotiline, metralindole, mianserin, mirtazepine, adinazolam, amitriptyline, amitriptylinoxide, amoxapine, butriptyline, clomipramine, demexiptiline, desipramine, dibenzepin, dimetacrine, dothiepin, doxepin, fluacizine, imipramine, imipramine N-oxide, iprindole, lofepramine, melitracen, metapramine, nortriptyline, noxiptilin, opipramol, pizotyline, propizepine, protriptyline, quinupramine, tianeptine, trimipramine, adrafinil, benactyzine, bupropion, butacetin, dioxadrol, duloxetine, etoperidone, febarbamate, femoxetine, fenpentadiol, fluoxetine, fluvoxamine, hematoporphyrin, hypericin, levophacetoperane, medifoxamine, milnacipran, minaprine, moclobemide, nefazodone, oxaflozane, piberaline, prolintane, pyrisuccideanol, ritanserin, roxindole, rubidium chloride, sulpiride, tandospirone, thozalinone, tofenacin, toloxatone, tranylcypromine, L-tryptophan, venlafaxine, viloxazine, and zimeldine.

Monophosphorylated prodrugs of acyclovir or a pharmaceutically acceptable salt, solvate, hydrate can be administered or formulated in combination with an antifungal agent. Suitable antifungal agents include but are not limited to amphotericin B, itraconazole, ketoconazole, fluconazole, intrathecal, flucytosine, miconazole, butoconazole, clotrimazole, nystatin, terconazole, tioconazole, ciclopirox, econazole, haloprogin, naftifine, terbinafine, undecylenate, and griseofuldin.

Monophosphorylated prodrugs of acyclovir or a pharmaceutically acceptable salt, solvate, hydrate can be administered or formulated in combination with an anti-inflammatory agent. Useful anti-inflammatory agents include, but are not limited to, non-steroidal anti-inflammatory drugs such as salicylic acid, acetylsalicylic acid, methyl salicylate, diflunisal, salsalate, olsalazine, sulfasalazine, acetaminophen, indomethacin, sulindac, etodolac, mefenamic acid, meclofenamate sodium, tolmetin, ketorolac, dichlofenac, ibuprofen, naproxen, naproxen sodium, fenoprofen, ketoprofen, flurbinprofen, oxaprozin, piroxicam, meloxicam, ampiroxicam, droxicam, pivoxicam, tenoxicam, nabumetome, phenylbutazone, oxyphenbutazone, antipyrine, aminopyrine, apazone and nimesulide; leukotriene antagonists including, but not limited to, zileuton, aurothioglucose, gold sodium thiomalate and auranofin; steroids including, but not limited to, alclometasone diproprionate, amcinonide, beclomethasone dipropionate, betametasone, betamethasone benzoate, betamethasone diproprionate, betamethasone sodium phosphate, betamethasone valerate, clobetasol proprionate, clocortolone pivalate, hydrocortisone, hydrocortisone derivatives, desonide, desoximatasone, dexamethasone, flunisolide, flucoxinolide, flurandrenolide, halcinocide, medrysone, methylprednisolone, methprednisolone acetate, methylprednisolone sodium succinate, mometasone furoate, paramethasone acetate, prednisolone, prednisolone acetate, prednisolone sodium phosphate, prednisolone tebuatate, prednisone, triamcinolone, triamcinolone acetonide, triamcinolone diacetate, and triamcinolone hexacetonide; and other anti-inflammatory agents including, but not limited to, methotrexate, colchicine, allopurinol, probenecid, sulfinpyrazone and benzbromarone.

Monophosphorylated prodrugs of acyclovir or a pharmaceutically acceptable salt, solvate, hydrate can be administered or formulated in combination with an immunomodulatory agent. Immunomodulatory agents include, but are not limited to, methothrexate, leflunomide, cyclophosphamide, cyclosporine A, mycophenolate mofetil, rapamycin (sirolimus), mizoribine, deoxyspergualin, brequinar, malononitriloamindes (e.g., leflunamide), T cell receptor modulators, and cytokine receptor modulators, peptide mimetics, and antibodies (e.g., human, humanized, chimeric, monoclonal, polyclonal, Fvs, ScFvs, Fab or F(ab)2 fragments or epitope binding fragments), nucleic acid molecules (e.g., antisense nucleic acid molecules and triple helices), small molecules, organic compounds, and inorganic compounds. Examples of T cell receptor modulators include, but are not limited to, anti-T cell receptor antibodies (e.g., anti-CD4 antibodies (e.g., cM-T412 (Boeringer), IDEC-CE9.1® (IDEC and SKB), mAB 4162W94, Orthoclone and OKTcdr4a (Janssen-Cilag)), anti-CD3 antibodies (e.g., Nuvion (Product Design Labs), OKT3 (Johnson & Johnson), or Rituxan (IDEC)), anti-CD5 antibodies (e.g., an anti-CD5 ricin-linked immunoconjugate), anti-CD7 antibodies (e.g., CHH-380 (Novartis)), anti-CD8 antibodies, anti-CD40 ligand monoclonal antibodies (e.g., IDEC-131 (IDEC)), anti-CD52 antibodies (e.g., CAMPATH 1H (Ilex)), anti-CD2 antibodies, anti-CD11a antibodies (e.g., Xanelim (Genentech)), and anti-B7 antibodies (e.g., IDEC-114 (IDEC)) and CTLA4-immunoglobulin. Examples of cytokine receptor modulators include, but are not limited to, soluble cytokine receptors (e.g., the extracellular domain of a TNF-.alpha. receptor or a fragment thereof, the extracellular domain of an IL-1.beta. receptor or a fragment thereof, and the extracellular domain of an IL-6 receptor or a fragment thereof), cytokines or fragments thereof (e.g., interleukin (IL)-2, IL-3, IL-4, IL-5, IL-6, IL-7, IL-8, IL-9, IL-10, IL-11, IL-12, IL-15, TNF-.alpha., interferon (IFN)-.alpha., IFN-.beta., IFN-.gamma., and GM-CSF), anti-cytokine receptor antibodies (e.g., anti-IFN receptor antibodies, anti-IL-2 receptor antibodies (e.g., Zenapax (Protein Design Labs)), anti-IL-4 receptor antibodies, anti-IL-6 receptor antibodies, anti-IL-10 receptor antibodies, and anti-IL-12 receptor antibodies), anti-cytokine antibodies (e.g., anti-IFN antibodies, anti-TNF-.alpha. antibodies, anti-IL-1.beta. antibodies, anti-IL-6 antibodies, anti-IL-8 antibodies (e.g., ABX-IL-8 (Abgenix)), and anti-IL-12 antibodies).

Monophosphorylated prodrugs of acyclovir or a pharmaceutically acceptable salt, solvate, hydrate can be administered or formulated in combination with cytokines. Examples of cytokines include, but are not limited to, interleukin-2 (IL-2), interleukin-3 (IL-3), interleukin-4 (IL-4), interleukin-5 (IL-5), interleukin-6 (IL-6), interleukin-7 (IL-7), interleukin-9 (IL-9), interleukin-10 (IL-10), interleukin-12 (IL-12), interleukin 15 (IL-15), interleukin 18 (IL-18), platelet derived growth factor (PDGF), erythropoietin (Epo), epidermal growth factor (EGF), fibroblast growth factor (FGF), granulocyte macrophage stimulating factor (GM-CSF), granulocyte colony stimulating factor (G-CSF), macrophage colony stimulating factor (M-CSF), prolactin, and interferon (IFN), e.g., IFN-alpha, and IFN-gamma).

Monophosphorylated prodrugs of acyclovir or a pharmaceutically acceptable salt, solvate, hydrate can be administered or formulated in combination with hormones. Examples of hormones include, but are not limited to, luteinizing hormone releasing hormone (LHRH), growth hormone (GH), growth hormone, releasing hormone, ACTH, somatostatin, somatotropin, somatomedin, parathyroid hormone, hypothalamic releasing factors, insulin, glucagon, enkephalins, vasopressin, calcitonin, heparin, low molecular weight heparins, heparinoids, synthetic and natural opioids, insulin thyroid stimulating hormones, and endorphins.

Monophosphorylated prodrugs of acyclovir or a pharmaceutically acceptable salt, solvate, hydrate can be administered or formulated in combination with .beta.-interferons which include, but are not limited to, interferon beta-1a and interferon beta-1b.

Monophosphorylated prodrugs of acyclovir or a pharmaceutically acceptable salt, solvate, hydrate can be administered or formulated in combination with an alkylating agent. Examples of alkylating agents include, but are not limited to nitrogen mustards, ethylenimines, methylmelamines, alkyl sulfonates, nitrosoureas, triazenes, mechlorethamine, cyclophosphamide, ifosfamide, melphalan, chlorambucil, hexamethylmelaine, thiotepa, busulfan, carmustine, streptozocin, dacarbazine and temozolomide.

Administration

In certain embodiments, monophosphorylated prodrugs of acyclovir or a pharmaceutically acceptable salt, solvate, hydrate is administered to the subject in a pharmaceutically-acceptable formulation. In certain embodiments, monophosphorylated prodrugs of acyclovir or a pharmaceutically acceptable salt, solvate, hydrate, or pharmaceutical composition is suitable for topical, intravenous, parental, or oral administration. The methods of the invention further include administering to a subject a therapeutically effective amount of monophosphorylated prodrugs of acyclovir or a pharmaceutically acceptable salt, solvate, hydrate, or a pharmaceutically acceptable salt, solvate, hydrate in combination with another pharmaceutically active compound. Pharmaceutically active compounds that may be used can be found in *Harrison's Principles of Internal Medicine*, Thirteenth Edition, Eds. T. R. Harrison et al. McGraw-Hill N.Y., N.Y.; and the Physicians Desk Reference 50th Edition 1997, Oradell N.J., Medical Economics Co., the complete contents of which are expressly incorporated herein by reference.

The phrase "pharmaceutically acceptable" refers to monophosphorylated prodrugs of acyclovir, compositions containing monophosphorylated prodrugs of acyclovir, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" includes pharmaceutically-acceptable material, composition or vehicle, involved in carrying or transporting the subject chemical from one organ, or portion of the body, to another organ, or portion of the body. Each carrier must be "acceptable" in the sense of being compatible with the other ingredients of the formulation and not injurious to the patient.

Methods of preparing these compositions include the step of bringing into association monophosphorylated prodrugs of acyclovir or a pharmaceutically acceptable salt, solvate, hydrate with the carrier and, optionally, one or more accessory ingredients. These compositions may also contain adjuvants such as preservatives, wetting agents, emulsifying agents and dispersing agents.

Regardless of the route of administration selected, monophosphorylated prodrugs of acyclovir, which may be used in a suitable salt, solvate, or hydrate form, and/or the pharmaceutical compositions of monophosphorylated prodrugs of acyclovir, are formulated into pharmaceutically acceptable dosage forms by conventional methods known to those of skill in the art.

Formulations are provided to a subject in an effective amount. The term "effective amount" includes an amount effective, at dosages and for periods of time necessary, to achieve the desired result. An effective amount of monophosphorylated prodrugs of acyclovir may vary according to factors such as the disease state, age, and weight of the subject, and the ability of the compound to elicit a desired response in the subject. Dosage regimens may be adjusted to provide the optimum therapeutic response.

The effective amount is generally determined by the physician on a case-by-case basis and is within the skill of one in the art. As a rule, the dosage for in vivo therapeutics or diagnostics will vary. Several factors are typically taken into account when determining an appropriate dosage. These factors include age, sex and weight of the patient, the condition being treated, and the severity of the condition.

Suitable dosages and formulations of monophosphorylated prodrugs of acyclovir or a pharmaceutically acceptable salt, solvate, hydrate can be empirically determined by the administering physician. Standard texts, such as Remington: The Science and Practice of Pharmacy, 17th edition, Mack Publishing Company, and the Physician's Desk Reference, each of which are incorporated herein by reference, can be consulted to prepare suitable compositions and doses for administration. A determination of the appropriate dosage is within the skill of one in the art given the parameters for use described herein.

Standard texts, such as Remington: The Science and Practice of Pharmacy, 17th edition, Mack Publishing Company, incorporated herein by reference, can be consulted to prepare suitable compositions and formulations for administration, without undue experimentation. Suitable dosages can also be based upon the text and documents cited herein. A determination of the appropriate dosages is within the skill of one in the art given the parameters herein.

In terms of treatment, an effective amount is an amount that is sufficient to palliate, ameliorate, stabilize, reverse or slow the progression of an enveloped virus infection, HIV infection, AIDS or the symptoms thereof. A therapeutically effective amount can be provided in one or a series of administrations. In terms of an adjuvant, an effective amount is one sufficient to enhance the immune response to the immunogen. The effective amount is generally determined by the physician on a case-by-case basis and is within the skill of one in the art.

As a rule, the dosage for in vivo therapeutics or diagnostics will vary. Several factors are typically taken into account when determining an appropriate dosage.

These factors include age, sex and weight of the patient, the condition being treated, the severity of the condition and the form of the antibody being administered. In an exemplary embodiment, the dosage of a monophosphorylated ACV prodrug is about 0.1 mg/kg/day to about 100 mg/kg/day, or about 0.5 mg/kg/day to about 50 mg/kg/day.

In certain embodiments, the subject is identified (i.e., diagnosed) as suffering from or susceptible to HIV infection (e.g., the subject has tested positive for HIV-1- or HIV-2 infection).

A therapeutically effective amount can be administered in one or more doses. The term "administration" or "administering" includes routes of introducing the compound(s) to a subject to perform their intended function. Examples of routes of administration which can be used include injection (subcutaneous, intravenous, parenterally, intraperitoneally, intrathecal), oral, inhalation, rectal and transdermal.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically", "peripheral administration" and "administered peripherally" as used herein mean the administration of a compound(s), drug or other material, such that it enters the patient's system and, thus, is subject to metabolism and other like processes, for example, subcutaneous administration.

Such dosages may vary, for example, depending on whether multiple administrations are given, tissue type and route of administration, the condition of the individual, the desired objective and other factors known to those of skill in the art.

Available routes of administration include subcutaneous, intramuscular, intraperitoneal, intradermal, oral, intranasal, intrapulmonary (i.e., by aerosol), intravenously, intramuscularly, subcutaneously, intracavity, intrathecally or transdermally, alone or in combination with other pharmaceutical agents.

Oral Dosage Forms

Monophosphorylated prodrugs of acyclov or a pharmaceutically acceptable salt, solvate, hydrate and compositions comprising monophosphorylated prodrugs of acyclovir that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, *Remington's Pharmaceutical Sciences,* 18th ed., Mack Publishing, Easton Pa. (1990).

Typical oral dosage forms of the invention are prepared by combining the active ingredient(s) in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms of the invention include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., nos. 2208, 2906, 2910), microcrystalline cellulose, and mixtures thereof.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions of the invention is typically present in from about 50 to about 99 weight percent of the pharmaceutical composition or dosage form.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. A specific binder is a mixture of microcrystalline cellulose and sodium carboxymethyl cellulose sold as AVICEL RC-581. Suitable anhydrous or low moisture excipients or additives include AVICEL-PH-103.TM and Starch 1500 LM.

Disintegrants are used in the compositions of the invention to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms of the invention. The amount of disintegrant used varies based upon the type of formulation, and is readily discernible to those of ordinary skill in the art. Typical pharmaceutical compositions comprise from about 0.5 to about 15 weight percent of disintegrant, specifically from about 1 to about 5 weight percent of disintegrant.

Disintegrants that can be used in pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, pre-gelatinized starch, other starches, clays, other algins, other celluloses, gums, and mixtures thereof.

Lubricants that can be used in pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W. R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

Parenteral and Intravascular Dosage Forms

Parenteral and intravascular dosage forms can be administered to patients by various routes including, but not limited to, subcutaneous, intravenous (including bolus injection and constant infusion), intramuscular, and intraarterial. Because their administration typically bypasses patients' natural defenses against contaminants, parenteral and intravascular dosage forms are preferably sterile or capable of being sterilized prior to administration to a patient. Examples of parenteral dosage forms include, but are not limited to, solutions ready for injection, dry products (including, but not limited to lyophilized powders, pellets, and tablets) ready to be dissolved or suspended in a pharmaceutically acceptable vehicle for injection, suspensions ready for injection, and emulsions.

Suitable vehicles that can be used to provide parenteral dosage forms of the invention are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms of the invention.

For intravascular administration, for instance by direct injection into the blood vessel, or surrounding area, it may be desirable to administer the compositions locally to the area in need of treatment. This can be achieved, for example, by local infusion during surgery, by injection, by means of a catheter, or by means of an implant, said implant being of a porous, non-porous, or gelatinous material, including membranes, such as silastic membranes, or fibers. A suitable such membrane is Gliadel® provided by Guilford Pharmaceuticals Inc.

Transdermal, Topical, And Mucosal Dosage Forms

Transdermal, topical, and mucosal dosage forms of the invention include, but are not limited to, ophthalmic solutions, sprays, aerosols, creams, lotions, ointments, gels, solutions, emulsions, suspensions, or other forms known to one of skill in the art. See, e.g., Remington's Pharmaceutical Sciences, 16th and 18th eds., Mack Publishing, Easton Pa. (1980 & 1990); and Introduction to Pharmaceutical Dosage Forms, 4th ed., Lea & Febiger, Philadelphia (1985). Dosage forms suitable for treating mucosal tissues within the oral cavity can be formulated as mouthwashes or as oral gels. Further, transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal, topical, and mucosal dosage forms encompassed by this invention are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof to form lotions, tinctures, creams, emulsions, gels or ointments, which are non-toxic and pharmaceutically acceptable. Moisturizers or humectants can also be added to pharmaceutical compositions and dosage forms if desired. Examples of such additional ingredients are well known in the art. See, e.g., Remington's Pharmaceutical Sciences, 16th and 18th eds., Mack Publishing, Easton Pa. (1980 & 1990).

Depending on the specific tissue to be treated, additional components may be used prior to, in conjunction with, or subsequent to treatment with active ingredients of the invention. For example, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as Tween 80 (polysorbate 80) and Span 60 (sorbitan monostearate).

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

Although methods and materials similar or equivalent to those described herein can be used in the practice of the present invention, certain specific methods and materials are described below. The materials, methods, and examples are illustrative only and not intended to be limiting. Other features and advantages of the invention will be apparent from the detailed description and from the claims.

Kits

This invention therefore encompasses kits which, when used by the medical practitioner, can simplify the identification of subjects and the administration of appropriate amounts of monophosphorylated prodrugs of acyclovir or a pharmaceutically acceptable salt, solvate, hydrate to a patient.

A typical kit of the invention comprises one or more unit dosage forms of monophosphorylated prodrugs of acyclovir or a pharmaceutically acceptable salt, solvate, hydrate and instructions for identification of a subject.

Kits of the invention can further comprise materials that are used to quantify the viral load for a herpes virus by quantitative real-time PCR or other methods known to those of skill in the art. Examples of such materials include, primers for HHV-1, HHV-2, HHV-3, HHV-4, HHV-5 HHV-6A, HHV-6B, HHV-7, HHV-8 and combinations thereof; reagents for performing a nucleic acid amplification reaction, for example, buffers, additional primers, positive and negative controls, nucleoside triphosphates, enzymes; and one or more suitable positive controls.

Kits of the invention can further comprise devices that are used to administer monophosphorylated prodrugs of acyclovir or a pharmaceutically acceptable salt, solvate, hydrate of the invention. Examples of such devices include, but are not limited to, intravenous cannulation devices, syringes, drip bags, patches, topical gels, pumps, containers that provide protection from photodegradation, autoinjectors, and inhalers.

Kits of the invention can further comprise pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

EXAMPLES

In order that the invention may be more fully understood, the following examples are provided. It should be understood that these examples are for illustrative purposes only and are not to be construed as limiting the invention in any way.

Methods

Synthesis of Compounds

I. Prodrugs Synthesis

Standard Procedure A: Synthesis of Dichlorophosphates

To a solution of phosphorus oxychloride (1.00 mol/eq) and the appropriate phenol or naphthol (1.00 mol/eq) in anhydrous diethyl ether stirred under an argon atmosphere, was added dropwise at −78° C. anhydrous TEA (1.00 mol/eq). Following the addition, the reaction mixture was stirred at −78° C. for 30 min, then at room temperature overnight. Formation of the desired compound was monitored by $^{31}P$ NMR. The mixture was filtered under nitrogen and the corresponding filtrate reduced to dryness to give the crude product as an oil.

Standard Procedure B: Synthesis of Phosphorochloridates

To a stirred solution of the appropriate aryl dichlorophosphate (1.00 mol/eq) and the appropriate amino acid ester salt (1.00 mol/eq) in anhydrous DCM was added, dropwise at −78° C. under an argon atmosphere, anhydrous TEA (2.00 mol/eq). Following the addition the reaction mixture was stirred at −78° C. for 1 h, then at room temperature for 2 h. Formation of the desired compound was monitored by $^{31}P$ NMR. After this period the solvent was removed under reduced pressure and the residue triturated with dry diethyl ether. The precipitate was filtered under nitrogen and the solution was concentrated to give an oil. Most of the aryl phosphorochloridates synthesised were purified by flash column chromatography (eluting with ethyl acetate/petroleum ether=60/40).

Standard Procedure C: Synthesis of Phosphoramidates ($^{t}$BuMgCl method)

To a stirring suspension/solution of acyclovir (1.00 mol/eq) in anhydrous THF was added dropwise under an argon atmosphere $^{t}$BuMgCl (2.00 mol/eq) and the reaction mixture was stirred at room temperature for 30 min. Then was added dropwise a solution of the appropriate phosphorochloridate (2.00-3.00 mol/eq) in anhydrous THF. The reaction mixture was stirred at room temperature overnight. The solvent was removed under reduced pressure and the residue was purified by column chromatography eluting with DCM/MeOH in different proportions.

Synthesis of 1-naphthyl dichlorophosphate

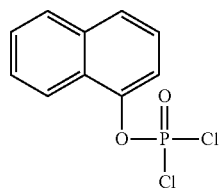 [SMILES: O=P(Cl)(Cl)Oc1cccc2ccccc12]

$C_{10}H_5Cl_2O_2P$
Mol Wt: 261.0411

To a stirred solution of 1-Naphthol (4.00 g, 27.74 mmol) and POCl$_3$ (2.59 mL, 27.74 mmol) in dry diethyl ether (60 mL), under an Argon atmosphere, dry TEA (3.87 mL, 27.74 mmol) was added dropwise, at −78° C. Following the addition, after 30 min at −78° C., the reaction mixture was stirred at room temperature overnight. After $^{31}P$ NMR, the solvent was removed under reduced pressure and the residue was triturated with dry diethyl ether. The precipitate was filtered, and the organic phase was removed under reduced pressure to give an oil (95%, 6.91 g).

$^{31}$P-NMR (CDCl$_3$, 202 MHz): δ 3.72.

$^{1}$H-NMR (CDCl$_3$, 500 MHz): δ 8.02-8.00 (1H, m, H-8), 7.81-7.80 (1H, m H-5), 7.72-7.70 (1H, m, H-4), 7.54-7.45 (4H, m, H-2, H-3, H-6, H-7).

Synthesis of 1-Naphthyl(benzoxy-dimethylglycinyl)-phosphorochloridate

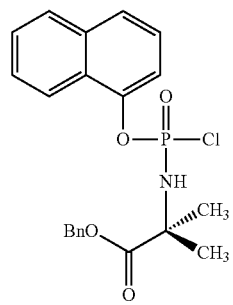

$C_{21}H_{21}ClNO_4P$
Mol Wt.: 417.8225

Prepared according to the Standard Procedure B, using 1-naphthyl phosphorochloridate (1.53 g, 5.88 mmol) and benzyl (dimethyglycine)hydrochloride (2.15 g, 5.88 mmol), anhydrous TEA (4.59 mL, 32.94 mmol) and anhydrous DCM (50 mL). The reaction was stirred at room temperature for 2 h. The crude product was obtained as an oil (33%, 0.80 g).

$^{31}$P-NMR (CDCl$_3$, 202 MHz): δ 5.78.

$^{1}$H-NMR (CDCl$_3$, 500 MHz): δ 8.03-7.28 (12H, m, Naph, OCH$_2$Ph), 5.16 (2H, s, OCH$_2$Ph), 1.76, 1.70 (6H, 2s, C(CH$_3$)$_2$).

Synthesis of 1-Naphthyl(benzoxy-L-alaninyl)-phosphorochloridate

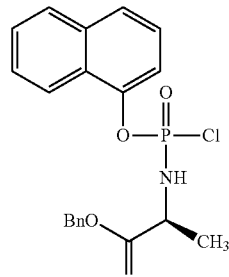

$C_{20}H_{19}ClNO_4P$
Mol Wt.: 403.7959

Prepared according to Standard Procedure B, 1-Naphtyl dichlorophosphate (6.91 g, 26.48 mmol), benzyl L-alanine hydrochloride (9.30 g, 26.48 mmol), anhydrous TEA (7.40 mL, 52.96 mmol) in anhydrous DCM (100 mL). The reaction mixture was stirred at −78° C. for 1 h, then at room temperature for 2 h. The crude was purified by column chromatography eluting with ethyl acetate/hexane=5/5 to give an oil (72%, 7.68 g).

$^{31}$P-NMR (CDCl$_3$, 202 MHz): δ 8.14, 7.88.
$^1$H-NMR (CDCl$_3$, 500 MHz): δ 7.99-7.25 (12H, m, Naph, OCH$_2$Ph), 5.15-5.07 (2H, m, CH$_2$Ph), 4.30-4.23 (1H, m, CHCH$_3$), 1.49-1.46 (3H, m, CHCH$_3$).

Synthesis of phenyl-(benzoxy-L-alaninyl)-phosphorochloridate

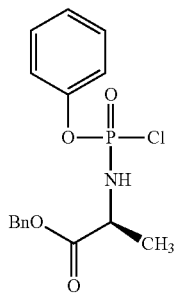

C$_{16}$H$_{17}$ClNO$_4$P
Mol Wt.: 353.7372

Prepared according to Standard Procedure B, using phenyl dichlorophosphate (0.30 mL, 2.00 mmol), benzyl L-alanine hydrochloride (0.43 g, 2.00 mmol), anhydrous TEA (0.56 mL, 4.00 mmol) in anhydrous DCM (15 mL). The reaction mixture was stirred at −78° C. for 1 h, then at room temperature for 3.5 h. The crude was obtained as an oil (87%, 0.62 g).

$^{31}$P-NMR (CDCl$_3$, 202 MHz): δ 7.86, 7.52.
$^1$H-NMR (CDCl$_3$, 500 MHz): δ 7.33-7.28 (10H, m, PhO, OCH$_2$Ph), 5.15-5.13 (2H, m, OCH$_2$Ph), 4.18-4.13 (1H, m, CHNH), 1.46-1.44 (3H, m, CH$_3$).

Synthesis of phenyl-(methoxy-L-alaninyl)-phosphorochloridate

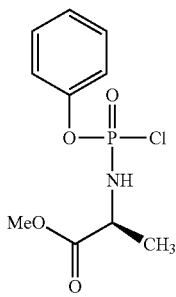 [SMILES: COC(=O)[C@H](C)NP(=O)(Cl)Oc1ccccc1]

C$_{10}$H$_{13}$ClNO$_4$P
Mol Wt.: 277.6413

Prepared according to Standard Procedure B, from phenyl dichlorophosphate (2.24 mL, 15.00 mmol), methyl L-alanine hydrochloride (2.09 g, 15.00 mmol), anhydrous TEA (4.20 mL, 30.00 mmol) and anhydrous DCM (80 mL). The reaction mixture was stirred at −78° C. for 30 min, then at room temperature for 2.5 h. The crude was purified by column chromatography eluting with ethyl acetate/hexane=6/4 to give an oil (81%, 3.35 g).

$^{31}$P-NMR (CDCl$_3$, 202 MHz): δ 7.95, 7.66.
$^1$H-NMR (CDCl$_3$, 500 MHz): δ 7.32-7.15 (5H, m, PhO), 4.42-4.34 (1H, m, NH), 4.17-4.08 (1H, m, CHNH), 3.72, 3.70 (3H, 2s, CH$_3$O), 1.45-1.43 (3H, m, CHCH$_3$).

Synthesis of 1-Naphthyl(methoxy-L-alaninyl)-phosphorochloridate

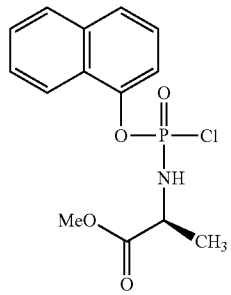 [SMILES: COC(=O)[C@H](C)NP(=O)(Cl)Oc1cccc2ccccc12]

C$_{14}$H$_{15}$ClNO$_4$P
Mol Wt.: 327.7000

Prepared according to Standard Procedure B, 1-naphthyl dichlorophosphate (2.00 g, 7.66 mmol), methyl L-alanine hydrochloride (1.07 g, 7.66 mmol), anhydrous TEA (2.14 mL, 15.32 mmol) in anhydrous DCM (45 mL). The reaction mixture was stirred at −78° C. for 1 h, then at room temperature for 2 h. The crude was purified by column chromatography eluting with ethyl acetate/hexane=6/4 to give an oil (61%, 1.54 g).

$^{31}$P-NMR (CDCl$_3$, 202 MHz): δ 8.14, 7.88.
$^1$H-NMR (CDCl$_3$, 500 MHz): δ 8.01-7.35 (7H, m, Naph), 4.33-4.27 (1H, m, NH), 4.26-4.20 (1H, m, CHNH), 3.74, 3.69 (3H, 2s, CH$_3$O), 1.50-1.46 (3H, m, CHCH$_3$).

Synthesis of 1-Naphthyl(benzoxy-L-phenylalaninyl)-phosphorochloridate

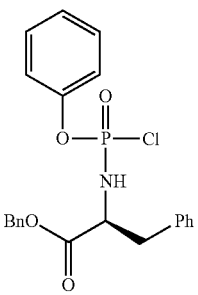 [SMILES: O=C(OCc1ccccc1)[C@H](Cc1ccccc1)NP(=O)(Cl)Oc1ccccc1]

C$_{22}$H$_{21}$ClNO$_4$P
Mol Wt.: 429.8332

Prepared according to Standard Procedure B, from phenyl dichlorophosphate (1.81 g, 8.57 mmol), benzyl L-phenylalanine hydrochloride (2.50 g, 8.57 mmol), anhydrous TEA (2.40 mL, 17.13 mmol) and anhydrous DCM (80 mL). The reaction mixture was stirred at −78° C. for 30 min, then at room temperature for 2 h. The crude was purified by column chromatography eluting with ethyl acetate/hexane=6/4 to give an oil (58%, 2.15 g).

$^{31}$P-NMR (CDCl$_3$, 202 MHz): δ 7.80, 7.77.

¹H-NMR (CDCl₃, 500 MHz): δ 7.32-6.91 (15H, m, PhO, CHCH₂Ph, OCH₂Ph), 5.08-5.07 (2H, m, OCH₂Ph), 4.46-4.33 (1H, m, CHNH), 3.12-3.01 (2H, m, CHCH₂Ph).

Synthesis of N²-DMF acyclovir (N'-(9-((2-hydroxyethoxy)methyl)-6-oxo-6,9-dihydro-1H-purin-2-yl)-N,N-dimethylformimidamide)

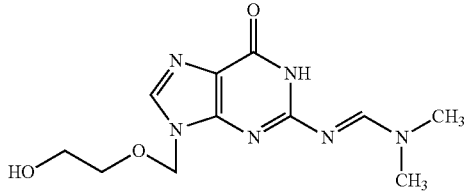 [SMILES: CN(C)/C=N/c1nc2c(ncn2COCCO)c(=O)[nH]1]

C₁₁H₁₆N₆O₃
Mol Wt.: 280.2831

To a suspension of acyclovir (1.00 g, 4.44 mmol) in dry DMF (20 mL) was added N,N-dimethylformamide dimethyl acetal (2.96 mL, 22.2 mmol) and the reaction mixture was stirred at room temperature for 1 day. After this period the suspension was filtered, and the solid was washed with diethyl ether to give a white solid (97%, 1.20 g).

¹H-NMR (DMSO 500 MHz): δ 11.30 (1H, s, NH), 8.58 (1H, s, H-8), 7.94 (1H, s, CHN(CH₃)₂), 5.45 (2H, s, H-1'), 4.65 (1H, t, OH), 3.52-3.49 (4H, m, H-4', H-5'), 3.17, 3.04 (6H, 2s, N(CH₃)₂).

Synthesis of N²-DMF acyclovir-[1-naphthyl(benzoxy-dimethylglycinyl)]phosphate

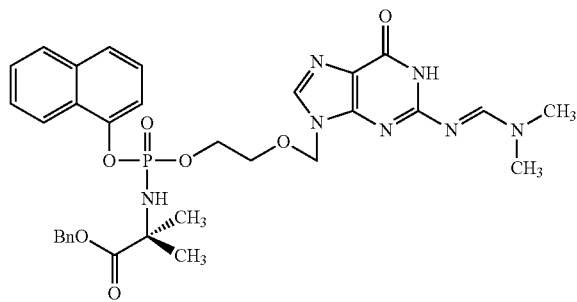

C₃₂H₃₆N₇O₇P
Mol Wt.: 661.6447

Prepared according to Standard Procedure C, from N²-DMF acyclovir (0.20 g, 0.72 mmol) in anhydrous THF (10 mL), ᵗBuMgCl (1.0 M THF solution, 0.86 mL, 0.86 mmol), 1-Naphthyl(benzoxy-dimethylglycinyl)-phosphorochloridate (0.80 g, 1.92 mmol) and the mixture reaction was stirred at room temperature overnight. Then ᵗBuMgCl (1.0 M THF solution, 0.58 mL, 0.58 mmol), was added, and after 3 h the solution was concentrated. The residue was purified by column chromatography eluting with DCM/MeOH=93/7, to give a white solid (35%, 0.17 g).

³¹P-NMR (MeOD, 202 MHz): δ 2.44, 2.41.
¹H-NMR (MeOD, 500 MHz): δ 8.13, 7.09 (14H, m, NCHN(CH₃)₂, H-8, Naph, OCH₂Ph), 5.34-5.24 (2H, 2s, H-1'), 4.99-4.92 (2H, m, OCH₂Ph), 4.05-3.99 (2H, m, H-5'), 3.65-3.52 (2H, m, H-4'), 2.86-2.83 (6H, 2s, N(CH₃)₂), 1.38-1.34 (6H, m, NHC(CH₃)₂).

Synthesis of acyclovir-[1-naphthyl(benzoxy-dimethylglycinyl)]phosphate Cf2573

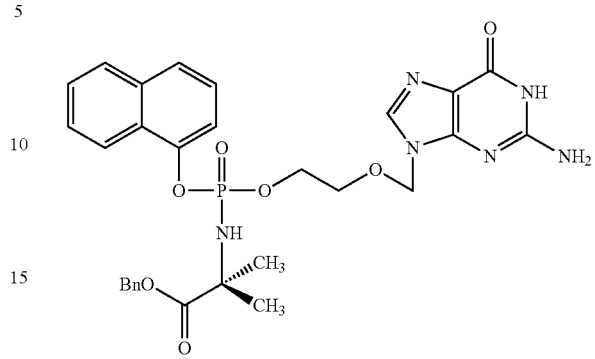

C₂₉H₃₁N₆O₇P
Mol Wt.: 606.5662

A solution of N²-DMF acyclovir-[1-naphthyl(benzoxy-dimethylglycinyl)]phosphate (0.17 g, 0.26 mmol) in n-propanol (4 mL) was stirred under reflux for 27 h. The solvent was then removed under reduced pressure and the residue was purified by column chromatography eluting with DCM/MeOH=95/5, to give a white solid (10%, 0.017 g).

³¹P-NMR (MeOD, 202 MHz): δ 2.42.
¹H-NMR (MeOD, 500 MHz): δ 8.17-8.12 (1H, m, H-8 Naph), 7.86-7.84 (1H, m, H-6 Naph), 7.75 (1H, s, H-8), 7.65 (1H, d, H-2 Naph), 7.56-7.23 (9H, m, Naph, OCH₂Ph), 5.35 (2H, s, H-1'), 5.13-5.06 (2H, m, OCH₂Ph), 4.19-4.14 (2H, m, H-5'), 3.68-3.66 (2H, m, H-4'), 1.49, 1.48 (6H, 2s, NHC(CH₃)₂).

Synthesis of N²-DMF acyclovir-[1-naphthyl(benzoxy-L-alaninyl)]phosphate

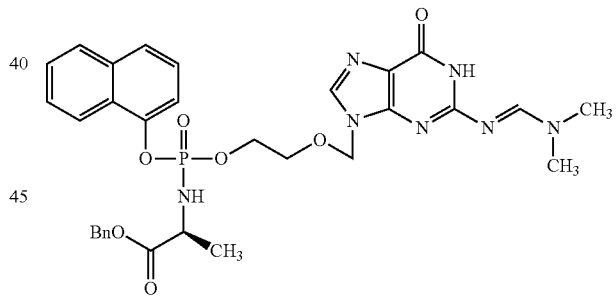

C₃₁H₃₄N₇O₇P
Mol Wt.: 647.6181

Prepared according to Standard Procedure C, from N²-DMF acyclovir (0.30 g, 1.08 mmol) in anhydrous THF (10 mL), ᵗBuMgCl (1.0 M THF solution, 2.16 mL, 2.16 mmol), 1-Naphthyl(benzoxy-L-alaninyl)-phosphorochloridate (1.31 g, 3.25 mmol) in anhydrous THF (10 mL) and the reaction mixture was stirred at room temperature overnight. The residue was purified by column chromatography, eluting with DCM/MeOH=95/5, to give a white solid (17%, 0.12 g).

³¹P-NMR (MeOD, 202 MHz): δ 4.18, 3.92.
¹H-NMR (MeOD, 500 MHz): δ 8.47, 8.46 (1H, 2s, NCHN (CH₃)₂), 8.01-7.98 (1H, m, H-8 Naph), 7.78-7.74 (2H, m, H-8, H-6 Naph), 7.56, 7.55 (1H, m, H-2 Naph), 7.41-7.12 (9H, m, Naph, OCH₂Ph), 5.37-5.36 (2H, 2s, H-1'), 5.00-4.93 (2H, m, OCH₂Ph), 4.14-4.06 (2H, m, H-5'), 3.96-3.88 (1H, m, CHCH₃), 3.88-3.59 (2H, m, H-4'), 2.95-2.93 (6H, m, N(CH₃)₂), 1.20-1.17 (3H, m, CHCH₃).

Synthesis of acyclovir-[1-naphthyl(benzoxy-L-alaninyl)]phosphate. Cf2574

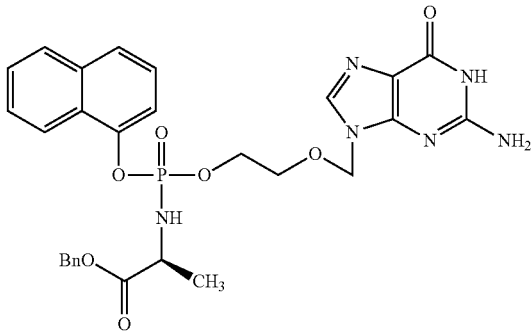

C$_{28}$H$_{29}$N$_6$O$_7$P
Mol Wt.: 592.5396

A solution of N$^2$-DMF acyclovir-[1-naphthyl(benzoxy-L-alaninyl)]phosphate (0.10 g, 0.16 mmol) in 2-propanol (5 mL) was stirred under reflux for 2 days. The solvent was then removed under reduced pressure and the residue was purified by column chromatography eluting with DCM/MeOH=96/4. The product was purified by preparative TLC (gradient elution of DCM/MeOH=99/1, then 98/2, then 96/4) to give a white solid (35%, 0.032 g).

$^{31}$P-NMR (MeOD, 202 MHz): δ 4.13, 3.96.
$^1$H-NMR (MeOD, 500 MHz): δ 8.01-7.99 (1H, m, H-8 Naph), 7.77-7.75 (1H, m, H-6 Naph), 7.67, 7.64 (1H, 2s, H-8), 7.58-7.13 (10H, m, Naph, OCH$_2$Ph), 5.28, 5.25 (2H, 2s, H-1'), 4.99-4.94 (2H, m, OCH$_2$Ph), 4.12-4.06 (2H, m, H-5'), 3.97-3.93 (1H, m, CHCH$_3$), 3.64-3.59 (2H, m, H-4'), 1.24-1.20 (3H, m, CHCH$_3$).
$^{13}$C-NMR (MeOD, 125 MHz): δ 20.29, 20.35, 20.40, 20.46 (CH$_3$), 51.76, 51.81 (CHCH$_3$), 67.19, 67.23, 67.30, 67.95, 67.98 (OCH$_2$Ph, C-5'), 69.31, 69.37, 69.43 (C-4'), 73.65 (C-1'), 116.26, 116.29, 116.35, 122.69, 122.80, 125.92, 126.51, 127.20, 127.42, 127.46, 127.74, 128.81, 128.83, 129.27, 129.33, 129.52, 129.57 (C-5, C-2 Naph, C-3 Naph, C-4 Naph, C-5 Naph, C-6 Naph, C-7 Naph, C-8 Naph, C-8a Naph, OCH$_2$Ph), 136.26, 137.23 (C-4a Naph, 'ipso' OCH$_2$Ph), 139.69 (C-8), 147.98, 148.04 ('ipso' Naph, C-4), 152.44 (C-2), 159.39 (C-6), 174.61, 174.88 (COOCH$_2$Ph).
EI MS=615.17 (M+Na).

Synthesis of acyclovir-[1-naphthyl(n-propoxy-L-alaninyl)]phosphate. Cf2629

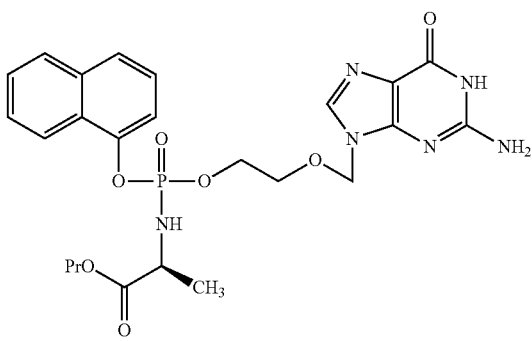

C$_{24}$H$_{29}$N$_6$O$_7$P
Mol Wt.: 544.4968

A solution of the protected precursor (0.78 g, 1.20 mmol) in n-propanol (28 mL) was stirred under reflux for 18 h. The solvent was then removed under reduced pressure and the residue was purified by column chromatography eluting with DCM/MeOH=95/5, to give a white solid (3%, 0.020 g).

$^{31}$P-NMR (DMSO, 202 MHz): δ 4.09, 4.01.
$^1$H-NMR (DMSO, 500 MHz): δ 10.68 (1H, bs, NH), 8.16-8.12 (1H, m, H-8 Naph), 8.01-7.99 (1H, m, H-6 Naph), 7.86, 7.85 (1H, 2s, H-8), 7.79-7.50 (5H, m, Naph), 6.55 (2H, bs, NH$_2$), 6.20-6.14 (1H, m, NHCH), 5.41, 5.40 (2H, 2s, H-1'), 4.22-4.17 (2H, m, H-5'), 4.00-3.93 (3H, m, CHCH$_3$+ OCH$_2$CH$_2$CH$_3$), 3.77-3.74 (2H, m, H-4'), 1.61-1.50 (2H, m, OCH$_2$CH$_2$CH$_3$), 1.31-1.27 (3H, m, CHCH$_3$), 0.90-0.84 (3H, m, OCH$_2$CH$_2$CH$_3$).
$^{13}$C-NMR (DMSO, 125 MHz): δ 10.07 (CH$_3$CH$_2$CH$_2$), 19.65, 19.72, 19.77 (CHCH$_3$), 21.36, 21.39 (CH$_3$CH$_2$CH$_2$), 49.81, 49.89 (CHCH$_3$), 64.87, 65.11, 65.14 (C-5'), 65.86, 65.90 (OCH$_2$CH$_2$CH$_3$), 67.57, 67.63 (C-4'), 71.84 (C-1'), 114.76, 116.48, 121.45, 121.51, 124.08, 125.64, 125.99, 126.04, 126.17, 126.24, 126.61, 127.64, 127.96, 128.32 (C-5, C-2 Naph, C-3 Naph, C-4 Naph, C-5 Naph, C-6 Naph, C-7 Naph, C-8 Naph, C-8a Naph), 134.21 (C-4a Naph), 137.57 (C-8), 146.46, 146.51 ('ipso' Naph), 151.36 (C-4), 153.88 (C-2), 156.73 (C-6), 173.13, 173.17, 173.32 (COOCH$_2$CH$_2$CH$_3$).
EI MS=567.17 (M+Na).

Synthesis of N$^2$-DMF acyclovir-[1-phenyl-(benzoxy-L-alaninyl)]phosphate

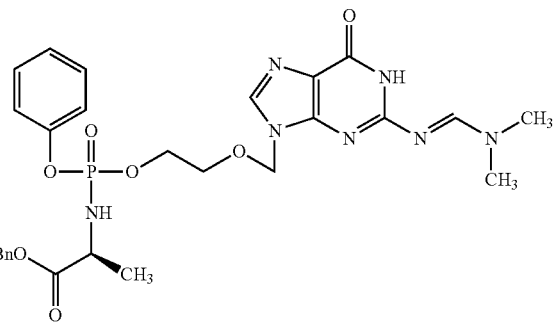

C$_{27}$H$_{32}$N$_7$O$_7$P
Mol Wt.: 597.5594

Prepared according to Standard Procedure C, from N$^2$-DMF ACV (0.40 g, 1.44 mmol) in anhydrous THF (15 mL), $^t$BuMgCl (1.0 M THF solution, 2.88 mL, 2.88 mmol), phenyl-(benzoxy-L-alaninyl)-phosphorochloridate (1.53 g, 4.32 mmol) in anhydrous THF (10 mL) and the reaction mixture was stirred at room temperature overnight. The residue was purified by column chromatography eluting with DCM/MeOH=95/5, to give a white solid (44%, 0.38 g).

$^{31}$P-NMR (MeOD, 202 MHz): δ 3.84, 3.47.
$^1$H-NMR (MeOD, 500 MHz): δ 8.54 (1H, s, NCHN(CH$_3$)$_2$), 7.80, 7.77 (1H, 2s, H-8), 7.26-7.14 (7H, m, PhO, OCH$_2$Ph), 7.05-7.00 (3H, m, PhO, OCH$_2$Ph), 5.41, 5.38 (2H, 2s, H-1'), 5.01, 4.99 (2H, 2s, OCH$_2$Ph), 4.08-4.05 (1H, m, H-5' of one diastereoisomer), 4.04-4.00 (1H, m, H-5' of one diastereoisomer), 3.86-3.81 (1H, m, CHCH$_3$), 3.66-3.61 (2H, m, H-4'), 3.03, 3.02 (3H, 2s, N(CH$_3$)$_2$), 2.97 (3H, s, N(CH$_3$)$_2$), 1.22-1.18 (3H, m, CHCH$_3$).

Synthesis of acyclovir-[1-phenyl-(benzoxy-L-alaninyl)]phosphate. Cf2648

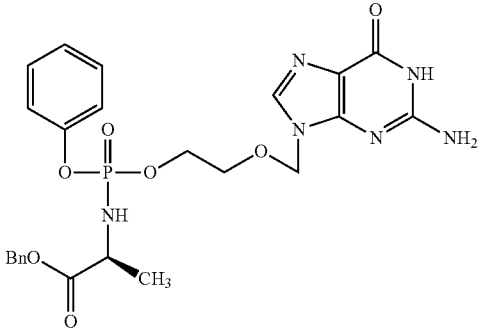 [SMILES: C[C@H](NP(=O)(OCCOCn1cnc2c(=O)[nH]c(N)nc21)Oc1ccccc1)C(=O)OCc1ccccc1]

C$_{24}$H$_{27}$N$_6$O$_7$P
Mol Wt.: 542.4809

A solution of N$^2$-DMF acyclovir-[1-phenyl-(benzoxy-L-alaninyl)]phosphate (0.38 g, 0.63 mmol) in 2-propanol (15 mL) was stirred under reflux for 40 h. The solvent was then removed under reduced pressure and the residue was purified by column chromatography gradient elution of DCM/MeOH=95/5 then 90/10. The product was purified by preparative TLC (gradient elution of DCM/MeOH=96/4 then 94/6) to give a white solid (14%, 0.048 g).

$^{31}$P-NMR (MeOD, 202 MHz): δ 3.80, 3.50.

$^1$H-NMR (MeOD, 500 MHz): δ 7.74-7.71 (1H, 2s, H-8), 7.23-7.14 (7H, m, PhO, OCH$_2$Ph), 7.06-7.01 (3H, m, PhO, OCH$_2$Ph), 5.32, 5.29 (2H, 2s, H-1'), 5.00-4.99 (2H, 2s, OCH$_2$Ph), 4.04-3.99 (2H, m, H-5'), 3.89-3.82 (1H, m, CHCH$_3$), 3.62-3.59 (2H, m, H-4'), 1.22, 1.21 (3H, 2d, CHCH$_3$).

$^{13}$C-NMR (MeOD, 125 MHz): δ 20.31, 20.37, 20.40, 20.45 (CH$_3$), 51.61, 51.73 (CHCH$_3$), 66.99, 67.03, 67.08, 67.12 (C-5'), 67.64, 67.97, 67.98 (OCH$_2$Ph), 69.40, 69.46 (C-4'), 73.76 (C-1'), 117.30, 121.39, 121.43, 121.47, 121.51, 126.08, 126.10, 129.19, 129.33, 129.36, 129.53, 129.58, 129.61, 130.19, 130.73 (C-5, PhO, OCH$_2$Ph), 137.27 ('ipso' OCH$_2$Ph), 139.75 (C-8), 152.11, 152.17 (C-4), 155.73 (C-2), 159.32 (C-6), 174.74, 174.78, 174.89, 174.92 (COOCH$_2$Ph).

EI MS=565.16 (M+Na)

Synthesis of N$^2$-DMF acyclovir-[1-phenyl-(methoxy-L-alaninyl)]phosphate

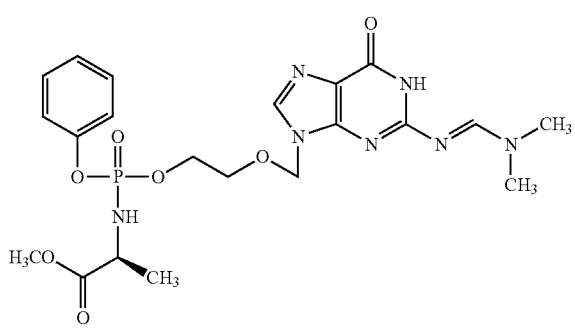 [SMILES: COC(=O)[C@H](C)NP(=O)(OCCOCn1cnc2c(=O)[nH]c(/N=C/N(C)C)nc21)Oc1ccccc1]

C$_{21}$H$_{28}$N$_7$O$_7$P
Mol Wt.: 521.4635

Prepared according to Standard Procedure C, from N$^2$-DMF ACV (0.40 g, 1.44 mmol) in anhydrous THF (15 mL), $^t$BuMgCl (1.0 M THF solution, 2.88 mL, 2.88 mmol), phenyl-(methoxy-L-alaninyl)-phosphorochloridate (1.20 g, 4.32 mmol) in anhydrous THF (10 mL) and the reaction mixture was stirred at room temperature overnight. The residue was purified by column chromatography gradient elution of DCM/MeOH=96/4 then 94/6, to give a white solid (36%, 0.27 g).

$^{31}$P-NMR (MeOD, 202 MHz): δ 3.76, 3.53.

$^1$H-NMR (MeOD, 500 MHz): δ 8.60 (1H, s, NCHN (CH$_3$)$_2$), 7.88, 7.86 (1H, 2s, H-8), 7.27-7.04 (3H, m, PhO), 6.97-6.90 (2H, m, PhO), 5.47, 5.45 (2H, 2s, H-1'), 4.15-4.12 (1H, m, H-5' of one diastereoisomer), 4.10-4.07 (1H, m, H-5' of one diastereoisomer), 3.85-3.78 (1H, m, CHCH$_3$), 3.74-3.66 (2H, m, H-4'), 3.58, 3.57 (3H, 2s, COOCH$_3$), 3.05, 3.01 (6H, 2s, N(CH$_3$)$_2$), 1.15-1.14 (3H, s, CHCH$_3$).

Synthesis of acyclovir-[1-phenyl-(methoxy-L-alaninyl)]phosphate. Cf1811

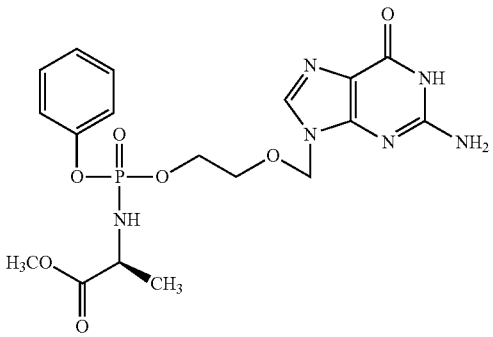 [SMILES: COC(=O)[C@H](C)NP(=O)(OCCOCn1cnc2c(=O)[nH]c(N)nc21)Oc1ccccc1]

C$_{18}$H$_{23}$N$_6$O$_7$P
Mol Wt.: 466.3850

A solution of N$^2$-DMF acyclovir-[1-phenyl-(methoxy-L-alaninyl)]phosphate (0.27 g, 0.52 mmol) in 2-propanol (10 mL) was stirred under reflux for 40 h. The solvent was then removed under reduced pressure and the residue was purified by column chromatography eluting with DCM/MeOH=95/5. The product was purified by preparative TLC (gradient elution of DCM/MeOH=95/5 then 94/6 then 92/8) to give a white solid (13%, 0.032 g).

$^{31}$P-NMR (MeOD, 202 MHz): δ 3.72, 3.55.

$^1$H-NMR (MeOD, 500 MHz): δ 7.87-7.85 (1H, 2s, H-8), 7.36-7.33 (2H, m, PhO), 7.20-7.16 (3H, m, PhO), 5.50, 5.47 (2H, 2s, H-1'), 4.27-417 (2H, m, H-5'), 3.97-3.90 (1H, m, CHCH$_3$), 3.84-3.78 (2H, m, H-4'), 3.69, 3.67 (3H, 2s, COOCH$_3$), 1.35-1.31 (3H, m, CHCH$_3$).

$^{13}$C-NMR (MeOD, 125 MHz): δ 20.33, 20.38, 20.42, 20.47 (CHCH$_3$), 51.45, 51.52 (CHCH$_3$), 52.72, 52.77 (COOCH$_3$), 66.99, 67.03, 67.09, 67.10, 67.13 (C-5'), 69.40, 69.44, 69.50 (C-4'), 73.68 (C-1'), 117.52, 121.10, 121.14, 121.32, 121.40, 121.42, 121.44, 121.45, 121.54, 121.58, 123.89, 126.07, 130.10, 130.25, 130.71 (C-5, PhO), 139.79 (C-8), 152.17, 152.22, 152.24, (C-4), 155.69 (C-2), 159.41 (C-6), 175.43, 175.47, 175.56, 175.59 (COOCH$_3$).

EI MS=489.13 (M+Na)

Synthesis of N²-DMF acyclovir-[1-naphthyl(methoxy-L-alaninyl)]phosphate

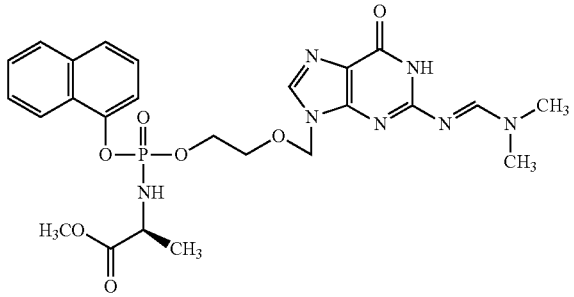 [SMILES: COC(=O)[C@H](C)NP(=O)(OCCOCn1cnc2c(=O)[nH]c(/N=C/N(C)C)nc21)Oc1cccc2ccccc12]

C₂₅H₃₀N₇O₇P
Mol Wt.: 571.5222

Prepared according to Standard Procedure C, from N²-DMF ACV (0.40 g, 1.44 mmol) in anhydrous THF (15 mL), ᵗBuMgCl (1.0 M THF solution, 2.88 mL, 2.88 mmol), 1-Naphthyl(methoxy-L-alaninyl)-phosphorochloridate (1.41 g, 4.32 mmol) in anhydrous THF (10 mL) and the reaction mixture was stirred at room temperature overnight. The residue was purified by column chromatography gradient elution of DCM/MeOH=96/4 then 94/6, to give a white solid (36%, 0.43 g).

³¹P-NMR (MeOD, 202 MHz): δ 4.09, 3.99.

¹H-NMR (MeOD, 500 MHz): δ 8.42 (1H, s, NCHN(CH₃)₂), 8.01-7.95 (1H, m, H-8 Naph), 7.79, 7.78 (1H, 2s, H-8), 7.73-7.18 (6H, m, Naph), 5.38, 5.36 (2H, 2s, H-1'), 4.20-4.12 (2H, m, H-5'), 3.89-3.82 (1H, m, CHCH₃), 3.72-3.66 (2H, m, H-4'), 3.48, 3.45 (3H, 2s, COOCH₃), 2.94, 2.90 (6H, 2s, N(CH₃)₂), 1.18-1.14 (3H, s, CHCH₃).

Synthesis of acyclovir-[1-naphthyl(methoxy-L-alaninyl)]phosphate. Cf2649

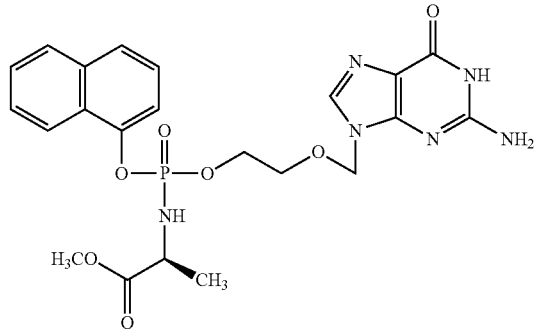 [SMILES: COC(=O)[C@H](C)NP(=O)(OCCOCn1cnc2c(=O)[nH]c(N)nc21)Oc1cccc2ccccc12]

C₂₂H₂₅N₆O₇P
Mol Wt.: 516.4437

A solution of N²-DMF acyclovir-[1-naphthyl(methoxy-L-alaninyl)]phosphate (0.41 g, 0.72 mmol) in 2-propanol (15 mL) was stirred under reflux for 72 h. The solvent was then removed under reduced pressure and the residue was purified by column chromatography gradient elution of DCM/MeOH=98/2 then 96/4 then 92/8. The product was purified by preparative TLC (gradient elution of DCM/MeOH=98/2 then 96/4 then 95/5) then by preparative reverse phase HPLC (gradient elution of H₂O/CH₃CN= from 100/0 to 0/100 in 45 min) to give a white solid (7%, 0.028 g).

³¹P-NMR (MeOD, 202 MHz): δ 4.07, 4.05.

¹H-NMR (MeOD, 500 MHz): δ 8.14-8.12 (1H, m, H-8 Naph), 7.88-7.87 (1H, m, H-6 Naph), 7.82, 7.81 (1H, 2s, H-8), 7.71-7.70 (1H, m, H-2 Naph), 7.56-7.51 (2H, m, H-5 Naph, H-7 Naph), 7.45-7.39 (2H, m, H-3 Naph, H-4 Naph), 5.44, 5.42 (2H, 2s, H-1'), 4.30-4.28 (1H, m, H-5' of one diastereoisomer), 4.27-4.24 (1H, m, H-5' of one diastereoisomer), 4.06-3.98 (1H, m, CHCH₃), 3.84-3.82 (1H, m, H-4' of one diastereoisomer), 3.80-3.79 (1H, m, H-4' of one diastereoisomer), 3.63, 3.59 (3H, 2s, COOCH₃), 1.34-1.30 (3H, m, CHCH₃).

¹³C-NMR (MeOD, 125 MHz): δ 20.35, 20.41, 20.47, 20.52 (CHCH₃), 51.59 (CHCH₃), 52.67, 52.76 (COOCH₃), 67.22, 67.26, 67.28, 67.32 (C-5'), 69.36, 69.42, 69.44, 69.50 (C-4'), 73.68 (C-1'), 116.23, 116.25, 116.28, 117.56, 122.69, 122.74, 125.90, 126.51, 127.42, 127.44, 127.75, 127.89, 127.94, 128.81, 128.83 (C-5, C-2 Naph, C-3 Naph, C-4 Naph, C-5 Naph, C-6 Naph, C-7 Naph, C-8 Naph, C-8a Naph), 136.26 (C-4a Naph), 139.69 (C-8), 148.00, 148.06 ('ipso' Naph), 153.38 (C-4), 155.80 (C-2), 159.57 (C-6), 175.44, 175.48, 175.58, 175.61 (COOCH₃).

EI MS=539.14 (M+Na)

Synthesis of N²-DMF acyclovir-[1-phenyl-(benzoxy-L-phenylalaninyl)]phosphate

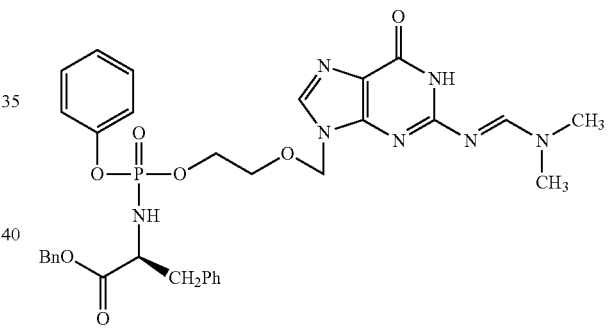

C₃₃H₃₆N₇O₇P
Mol Wt.: 673.6554

Prepared according to Standard Procedure C, from N²-DMF ACV (0.40 g, 1.44 mmol) in anhydrous THF (15 mL), ᵗBuMgCl (1.0 M THF solution, 2.88 mL, 2.88 mmol), 1-Naphthyl(benzoxy-L-phenylalaninyl)-phosphorochloridate (1.25 g, 2.88 mmol) in anhydrous THF (10 mL) and the reaction mixture was stirred at room temperature overnight. The residue was purified by column chromatography gradient elution of DCM/MeOH=98/2 then 95/5, to give a white solid (59%, 0.58 g).

³¹P-NMR (MeOD, 202 MHz): δ 3.39, 3.36.

¹H-NMR (MeOD, 500 MHz): δ 8.48, 8.47 (1H, 2s, NCHN(CH₃)₂), 7.74, 7.73 (1H, 2s, H-8), 7.19-6.86 (15H, m, PhO, COOCH₂Ph, CHCH₂Ph), 5.33, 5.32 (2H, 2s, H-1'), 4.95-4.90 (2H, m, COOCH₂Ph), 4.03-3.96 (1H, m, CHCH₃), 3.91-3.86 (0.5H, m, H-5' of one diastereoisomer), 3.81-3.67 (1.5H, m, H-5'), 3.54-3.48 (2H, m, H-4'), 2.96-2.87 (7H, m, N(CH₃)₂, CHCH₂Ph of one diastereoisomer), 2.76-2.71 (1H, m, CHCH₂Ph of one diastereoisomer).

Synthesis of acyclovir-[1-phenyl-(benzoxy-L-phenylalaninyl)]phosphate. Cf2650

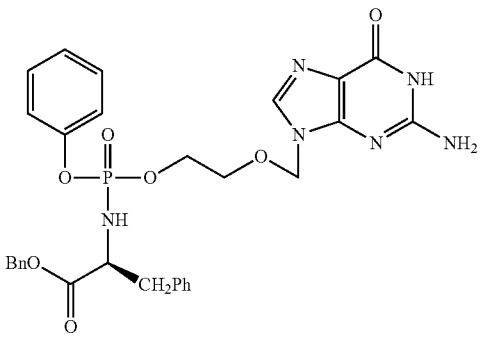

$C_{30}H_{31}N_6O_7P$
Mol Wt.: 618.5769

A solution of $N^2$-DMF acyclovir[1-phenyl-(benzoxy-L-phenylalaninyl)]phosphate (0.49 g, 0.73 mmol) in 2-propanol (20 mL) was stirred under reflux for 64 h. The solvent was then removed under reduced pressure and the residue was purified by column chromatography eluting with DCM/MeOH=95/5. The product was purified by preparative TLC (gradient elution of DCM/MeOH=98/2 then 96/4) to give a white solid (14%, 0.054 g).

$^{31}$P-NMR (MeOD, 202 MHz): δ 3.41, 3.31.
$^1$H-NMR (MeOD, 500 MHz): δ 7.65-7.64 (1H, 2s, H-8), 7.19-6.87 (15H, m, PhO, COOCH$_2$Ph, CHCH$_2$Ph), 5.25, 5.24 (2H, 2s, H-1'), 4.98-4.95 (2H, m, COOCH$_2$Ph), 4.06-3.97 (1H, m, CHCH$_3$), 3.89-3.84 (0.5H, m, H-5' of one diastereoisomer), 3.80-3.64 (1.5H, m, H-5'), 3.48 (2H, bs, H-4'), 2.97-2.90 (1H, m, CHCH$_2$Ph of one diastereoisomer), 2.78-2.73 (1H, m, CHCH$_2$Ph of one diastereoisomer).
$^{13}$C-NMR (MeOD, 125 MHz): δ 40.88, 40.93, 40.99 (CHCH$_2$Ph), 57.77, 57.91 (CHCH$_2$Ph), 66.87 (C-5'), 68.02, 68.03 (COOCH$_2$Ph), 69.25, 69.32 (C-4'), 73.64 (C-1'), 117.55, 121.30, 121.34, 121.37, 121.41, 126.00, 127.93, 129.37, 129.52, 129.54, 129.57, 130.62, 130.65, 130.68 (C-5, PhO, OCH$_2$Ph, CHCH$_2$Ph), 137.03, 138.02, 138.08 ('ipso' CHCH$_2$Ph, 'ipso' OCH$_2$Ph), 139.73 (C-8), 153.35 (C-4), 155.65 (C-2), 159.41 (C-6), 173.85 (COOCH$_2$Ph)
EI MS=641.19 (M+Na)

II. Effect of ACV Monophosphorylated Prodrugs on HIV Replication
A. Materials and Methods
Cells Human T-lymphocyte MT-4 or CEM cells were obtained from the American Type Culture Collection (Manassas, Va.) and cultivated in RPMI 1640 medium supplemented with 10% fetal bovine serum 2 mM L-glutamine and 0.075 M NaHCO$_3$.

Viruses

HIV-1(III$_B$) was provided by Dr. R. C. Gallo and Dr. M. Popovic (at that time at the NCI, National Institutes of Health, Bethesda). A closely related HIV-1 variant (LAI.04) was obtained from the NIH AIDS Reagent Program.

Antiretrovirus Assays a. In Cell Line

Briefly, CEM cells (4.5×10$^5$ cells per ml) were suspended in fresh culture medium and infected with HIV-1 at 100 CCID$_{50}$ (cell culture infective dose-50) per ml of cell suspension. Then 100 µl of the infected cell suspension were transferred to microplate wells, mixed with 100 µl of the appropriate dilutions of the test compounds, and further incubated at 37° C. After 4-5 days, giant cell formation was recorded microscopically in the CEM cell cultures. The 50% effective concentration (EC$_{50}$) corresponded to the compound concentrations required to prevent syncytium formation by 50% in the virus-infected CEM cell cultures. MT4 cells (1×10$^4$ cells per ml) were suspended in fresh culture medium and infected with 10 uL of HIV-1$_{LAI.04}$ viral stock at 260 CCID$_{50}$ (cell culture infective dose-50) per ml of cell suspension. Then infected cell suspensions were transferred to microplate wells, mixed with 1 mL of the appropriate dilutions of the test compounds, and further incubated at 37° C. After 7 days, p24 production was measured in the MT4 cell cultures supernatant. The 50% effective concentration (EC$_{50}$) corresponded to the compound concentrations required to suppress by 50% the production of p24 in the virus-infected MT4 cell cultures.

b. In Ex vivo Human Tonsillar Tissue Culture

Tonsillar tissues from routine surgery were obtained from the Children's National Medical Center, Washington D.C. Tissues were dissected into 2-mm$^3$ blocks and placed onto collagen sponge gels at the air-liquid interface. Tissue blocks were cultured in RPMI 1640 medium containing 15% heat-inactivated fetal calf serum, nonessential amino acids (1 mM), sodium pyruvate (1 mM), amphotericin B (2.5 µg/mL) and gentamicin (50 µg/mL). The culture medium was changed every 3 days and prodrugs were replenished. Blocks of human lymphoid tonsillar tissues were inoculated ex vivo with X4$_{LAI.04}$ and treated with increasing concentration of each prodrug (0,1; 0.5; 1; 5 and 10 µM). HIV-1 replication was monitored by measuring p24$_{gag}$ accumulated in culture media over 3 day periods. For each donor, HIV-1 replication in 9 treated blocks was compared with that in 9 untreated blocks from the same donor.

B. Results.
I. In Cell Lines
a. CEM Cell Line

Anti-HIV activity of prodrugs of ACV and Ganciclovir (GCV) in CEM cell cultures

TABLE 1

| Compound | EC$_{50}$ (µM) | | CC$_{50}$ (µM) |
| --- | --- | --- | --- |
| | HIV-1(III$_B$) | HIV-2(ROD) | |
| Cf 2574 | 17.5 | 7.3 | 17 |
| Cf 2629 | 3.4 | 7.4 | 22 |
| Cf 1811 | 16 | 26 | 67 |
| Cf 2648 | 3.2 | 8.8 | 33 |
| Cf 2649 | 9.7 | 9.3 | 57 |
| Cf 2650 | 24 | 21 | 42 |
| Cf 1810* | 30 | 83 | >100 |
| ACV | >250 | >250 | >250 |
| GCV | >250 | >250 | >250 |

EC$_{50}$ = 50% Effective concentration.
CC$_{50}$ = 50% Cytostatic concentration.
*GCV prodrug.

The ACV prodrugs were evaluated against HIV-1 replication in CEM and MT-4 cell cultures. In general, the ACV prodrugs inhibited virus-induced giant cell formation in the virus-infected CEM cell cultures. The propyl ester of the naphthylalaninyl phoshoramidate, Cf 2629 was most inhibitory for HIV-1 (EC$_{50}$=3.2 µM).

b. MT-4 Cell Line

Anti-HIV activity of prodrugs of ACV and ACV phosphorylated derivatives (ACV-monophosphate, ACV triphosphate) in MT4 cell cultures

TABLE 2

| Compound | EC$_{50}$ (μM) |
| --- | --- |
| Cf 2574 | 0.8 |
| Cf 2629 | 10 |
| Cf 1811 | 15 |
| Cf 2648 | 8 |
| Cf 2649 | 3 |
| Cf 2650 | 16 |
| ACV | >250 |
| ACV monophosphate | 100 |
| ACV triphosphate | 50 |

II. In Ex vivo Human Tonsillar Tissue

TABLE 3

| Compound | EC$_{50}$ (μM) | EC$_{75}$ (μM) | EC$_{90}$ (μM) |
| --- | --- | --- | --- |
| Cf 2574 | <0.1 | 0.62 | 0.9 |
| Cf 2629 | <0.1 | 0.4 | 1.5 |
| Cf 1811 | <0.1 | 0.1 | 0.5 |
| Cf 2648 | <0.1 | <0.1 | 0.55 |
| Cf 2649 | <0.1 | <0.1 | 0.1 |
| Cf 2650 | <0.1 | 1.5 | 3 |

See FIGS. 1 and 2 for the effect of Cf 2649 on HIV-1$_{LAI.04}$ replication

The contents of all references cited are incorporated herein by reference in their entirety.

EQUIVALENTS

Those skilled in the art will recognize, or be able to ascertain using no more than routine experimentation, many equivalents of the specific embodiments of the invention described herein. Such equivalents are intended with be encompassed by the following claims.

REFERENCES

1. Margolis, L. Cytokines—strategic weapons in germ warfare? *Nat Biotechnol* 21, 15-16 (2003).
2. Grivel, J. C. et al. Suppression of CCR5-but not CXCR4-tropic HIV-1 in lymphoid tissue by human herpesvirus 6. *Nat Med* 7, 1232-1235 (2001).
3. Xiang, J. et al. Effect of coinfection with GB virus C on survival among patients with HIV infection. *N Engl J Med* 345, 707-714 (2001).
4. Lisco, A. et al. Viral interactions in human lymphoid tissue: Human herpesvirus 7 suppresses the replication of CCR5-tropic human immunodeficiency virus type 1 via CD4 modulation. *J Virol* 81, 708-717 (2007).
5. Corey, L. Synergistic copathogens—HIV-1 and HSV-2. *N Engl J Med* 356, 854-856 (2007).
6. Elion, G. B. The biochemistry and mechanism of action of acyclovir. *J Antimicrob Chemother* 12 Suppl B, 9-17 (1983).
7. Reardon, J. E. & Spector, T. Herpes simplex virus type 1 DNA polymerase. Mechanism of inhibition by acyclovir triphosphate. *J Biol Chem* 264, 7405-7411 (1989).
8. St Clair, M. H., Furman, P. A., Lubbers, C. M. & Elion, G. B. Inhibition of cellular alpha and virally induced deoxyribonucleic acid polymerases by the triphosphate of acyclovir. *Antimicrob Agents Chemother* 18, 741-745 (1980).
9. De Clercq, E. et al. Antiviral agents active against human herpesviruses HHV-6, HHV-7 and HHV-8. *Rev Med Virol* 11, 381-395 (2001).
10. Grivel, J. C. et al. HIV-1 pathogenesis differs in rectosigmoid and tonsillar tissues infected ex vivo with CCR5- and CXCR4-tropic HIV-1. *Aids* 21, 1263-1272 (2007).
11. Glushakova, S., Baibakov, B., Margolis, L. B. & Zimmerberg, J. Infection of human tonsil histocultures: a model for HIV pathogenesis. *Nat Med* 1, 1320-1322 (1995).
12. Biancotto, A. et al. Abnormal activation and cytokine spectra in lymph nodes of people chronically infected with HIV-1. *Blood* 109, 4272-4279 (2007).
13. Soul-Lawton, J. et al. Absolute bioavailability and metabolic disposition of valaciclovir, the L-valyl ester of acyclovir, following oral administration to humans. *Antimicrob Agents Chemother* 39, 2759-2764 (1995).
14. Lusso, P. & Gallo, R. C. Human herpesvirus 6 in AIDS. *Lancet* 343, 555-556 (1994).
15. Balzarini, J., Haller-Meier, F., De Clercq, E. & Meier, C. Antiviral activity of cyclosaligenyl prodrugs of acyclovir, carbovir and abacavir. *Antivir Chem Chemother* 12, 301-306 (2001).
16. Talarico, C. L. et al. Acyclovir is phosphorylated by the human cytomegalovirus UL97 protein. *Antimicrob Agents Chemother* 43, 1941-1946 (1999).
17. Ioannidis, J. P. et al. Clinical efficacy of high-dose acyclovir in patients with human immunodeficiency virus infection: a meta-analysis of randomized individual patient data. *J Infect Dis* 178, 349-359 (1998).
18. Resnick, L., Markham, P. D., Veren, K., Salahuddin, S. Z. & Gallo, R. C. In vitro suppression of HTLV-III/LAV infectivity by a combination of acyclovir and suramin. *J Infect Dis* 154, 1027-1030 (1986).
19. Torres, R. A. et al. Acyclovir use and survival among human immunodeficiency virus-infected patients with CD4 cell counts of <500/mm3. The Terry Beirn Community Programs for Clinical Research on AIDS (CPCRA). *Clin Infect Dis* 26, 85-90 (1998).
20. Suligoi, B., Dorrucci, M., Volpi, A., Andreoni, M. & Rezza, G. No protective effect of acyclovir on HIV disease progression in a cohort of HSV-2-HIV-infected individuals. *Antivir Ther* 7, 289-291 (2002).
21. Schacker, T., Zeh, J., Hu, H., Shaughnessy, M. & Corey, L. Changes in plasma human immunodeficiency virus type 1 RNA associated with herpes simplex virus reactivation and suppression. *J Infect Dis* 186, 1718-1725 (2002).
22. Nagot, N. et al. Reduction of HIV-1 RNA levels with therapy to suppress herpes simplex virus. *N Engl J Med* 356, 790-799 (2007).
23. Zuckerman, R. A. HSV suppression with valacyclovir reduces rectal and blood plasma HIV-1 levels in HIV-1, HSV-2 seropositive men: A randomized, double-blind, placebo-controlled, crossover trial. *Journal of Infectious Disease* in press (2007).
24. Chen, T. & Hudnall, S. D. Anatomical mapping of human herpesvirus reservoirs of infection. *Mod Pathol* 19, 726-737 (2006).
25. De Bolle, L., Naesens, L. & De Clercq, E. Update on human herpesvirus 6 biology, clinical features, and therapy. *Clin Microbiol Rev* 18, 217-245 (2005).
26. Gorelick, R. J. et al. Noninfectious human immunodeficiency virus type 1 mutants deficient in genomic RNA. *J Virol* 64, 3207-3211 (1990).

We claim:
1. A compound represented by the formula (Formula I):

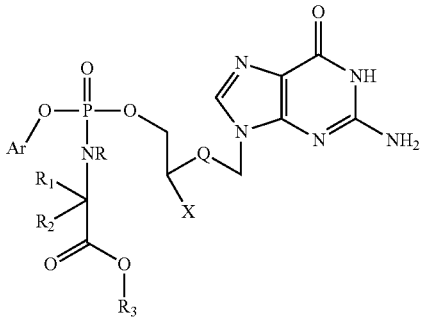

wherein:
- Ar is an aryl group having 6 to 30 carbon atoms or a heteroaryl group having 6 to 30 atoms, wherein the aryl or heteroaryl group may be substituted with 1-3 substituents;
- Q is O, S, or $CR_4R_5$, wherein $R_4$ and $R_5$ are independently selected from H and $C_1$-$C_6$ alkyl;
- X is H, or $CH_2OH$;
- $R_1$ and $R_2$ are independently selected from H, or the group consisting of optionally substituted $C_1$-$C_{20}$ alkyl, $C_2$-$C_{20}$ alkenyl, $C_{1-20}$ alkoxy, $C_2$-$C_{20}$ alkynyl, or $C_3$-$C_{20}$ cycloalkyl; or
- $R_1$ and $R_2$ are fused to form a contiguous carbocyclic or heterocyclic ring consisting of 3-20 carbons in total; and
- each of R and $R_3$ is independently selected from the group consisting of H, and optionally substituted $C_1$-$C_{20}$ alkyl, $C_3$-$C_{20}$ cycloalkyl, $C_2$-$C_{20}$ alkenyl, $C_{1-20}$ alkoxy, or $C_6$-$C_{30}$ alkynyl; or
- R and $R_1$ are taken together with the nitrogen and carbon atoms to which they are respectively attached to form a ring consisting of 4-6 C or N atoms;

pharmaceutically acceptable salts, amine prodrugs, ester prodrugs, carbamate and carbonate prodrugs, ureide prodrugs, and phosphate prodrugs thereof;

with the proviso that if Ar is phenyl, R is H, $R_1$ and $R_2$ differ and consist of a methyl and an H, X is H, $R_3$ is H or methyl, then Q cannot be O.

2. The compound of claim 1, wherein R and $R_1$ are taken together with the nitrogen and carbon atoms to which they are respectively attached to form a 5 membered ring.

3. The compound of claim 1, wherein Ar is phenyl, pyridinyl, pyrimidinyl, or naphthyl.

4. The compound of claim 1, wherein Ar is phenyl, or 1-naphthyl.

5. The compound of claim 1, wherein Ar is phenyl.

6. The compound of claim 1, wherein X is H.

7. The compound of claim 1, wherein Q is $CH_2$.

8. The compound of claim 1, wherein $R_3$ is optionally substituted $C_2$-$C_{20}$-alkyl or $C_3$-$C_{20}$ cycloalkyl.

9. The compound of claim 1, wherein $R_3$ is ethyl, n-propyl, i-propyl, t-butyl or benzyl.

10. The compound of claim 1, wherein $R_1$ is methyl.

11. The compound of claim 1, wherein the compound is acyclovir 5'-O-(1-naphthyl benzylalaninyl)phosphate, acyclovir 5'-O-(1-naphthyl n-propylalaninyl)phosphate, acyclovir 5'-O-(1-phenyl benzylalaninyl)phosphate, acyclovir 5'-O-(1-naphthyl methylalaninyl)phosphate, or acyclovir 5'-O-(1-phenyl benzylphenylalaninyl)phosphate.

12. A pharmaceutical formulation comprising a compound of claim 1, together with a pharmaceutically acceptable carrier.

* * * * *